United States Patent [19]

Futata et al.

[11] Patent Number: 5,194,134

[45] Date of Patent: Mar. 16, 1993

[54] GASEOUS CARBON DIOXIDE DETECTION SENSOR

[75] Inventors: Hozumi Futata; Takayuki Suzuki; Hironori Hadano; Hiromasa Takashima, all of Shizuoka; Noboru Yamazoe; Norio Miura, both of Fukuoka, all of Japan

[73] Assignee: Yazaki Corporation, Tokyo, Japan

[21] Appl. No.: 741,907

[22] Filed: Aug. 8, 1991

[30] Foreign Application Priority Data

Aug. 9, 1990 [JP] Japan .................. 2-209220
Dec. 6, 1990 [JP] Japan .................. 2-405324
Feb. 6, 1991 [JP] Japan .................. 3-35082
Mar. 28, 1991 [JP] Japan .................. 3-64652

[51] Int. Cl.$^5$ ........................ G01N 27/26
[52] U.S. Cl. .................. 204/421; 204/424; 204/427; 204/431; 204/432; 204/416; 204/419; 204/426
[58] Field of Search ............ 204/416, 419, 421, 424, 204/426, 427, 431, 432

[56] References Cited

U.S. PATENT DOCUMENTS 4,319,966 3/1982 Carlson et al. ............ 204/421
4,377,460 3/1983 Hirayama et al. .......... 204/195
4,715,944 12/1987 Yanagida et al. .......... 204/426

FOREIGN PATENT DOCUMENTS 0060944 9/1982
0182921 6/1986 European Pat. Off.

OTHER PUBLICATIONS

Solid State Ionics, vol. 24, No. 4, Sep. 1987, Amsterdam NL T. T. Maruyama et al: 'electromotive force of a CO—CO$_2$ sensor in CO—CO$_2$—H$_2$-H$_2$O atmospheres and simultaneous determination of partial pressures of CO— and CO$_2$'.

Primary Examiner—John Niebling
Assistant Examiner—Bruce F. Bell
Attorney, Agent, or Firm—Nikaido, Marmelstein, Murray & Oram

[57] ABSTRACT

A gaseous carbon dioxide detection sensor comprising a detection electrode and a reference electrode opposed on both sides of an ionic conductor, wherein a mixture comprising one mol of an alkali metal carbonate more than one mol of an alkaline earth metal carbonate is used as the detection material for the detection electrode. The detection sensor has the electromotive force characteristic relative to the gaseous carbon dioxide less undergoing the effect of moisture in the gas to be measured and has a high sensitivity.

4 Claims, 29 Drawing Sheets

GASEOUS CARBON DIOXIDE DETECTION SENSOR

BACKGROUND OF THE INVENTION

1. Field of the Invention

The present invention concerns a solid electrolyte type gaseous carbon dioxide sensor and, more in particular, it relates to an improvement of a humidity proof property for a detection electrode.

2. Description of the Prior Art

Solid electrolyte sensors under development at present usually comprise a detection electrode and a reference electrode disposed on both sides of a solid electrolyte as an ionic conductor.

Generally, in a case of detecting gaseous ingredients present in an atmosphere by using a solid electrolyte sensor, an ionic conductor in which specific ions are movable and, in combination with this specific ion conductor used as the solid electrolyte, a compound containing the specific ions and an aimed gaseous ingredient is used as a detection material being covered on an electrode, for example, made of platinum.

A gaseous carbon dioxide sensor based on such a principle uses, for example, a sodium ionic conductor such as of $\beta$-alumina (general formula: $Na_2O \cdot nAl_2O_3$, $n=5-11$) or NASICON (general formula: $Na_{1-x}Zr_2P_{3-x}Si_xO_{12}$). In this case, a platinum gauge covered with sodium carbonate or the like is used as a detection electrode.

A typical reference electrode comprises gold or platinum alone or being covered with sodium carbonate or the like which is tightly sealed in air or gaseous carbon dioxide. Accordingly, while gaseous carbon dioxide as a gas to be measured can be in contact with the detection electrode but not with the reference electrode on the opposite side.

The sensor portion is heated upon operation usually to a constant temperature of about 400° C. to 600° C., in which an electromotive force of sodium ions is caused to the detection electrode corresponding to the partial pressure of the gaseous carbon dioxide in a gas to be detected which is in contact with the detection electrode and sodium ions in proportion with the difference of the electromotive force between both of the electrodes conduct through the ionic conductor. Accordingly, the concentration of the gaseous carbon dioxide can be detected by measuring the electromotive force.

However, in a case of the existent gaseous carbon dioxide sensor using sodium carbonate as the detection material for the detection electrode and using NASICON for the ionic conductor as described above, the characteristic of the electromotive force greatly suffers from the effect of a moisture content in the gas to be detected. FIG. 3 shows the electromotive force characteristic of the device, heated to an element temperature of 550° C., relative to the change of concentration of gaseous carbon dioxide in air at a humidity of 20% and 75% as well as in an anhydrous state. As shown in the figure, if the air contains the moisture content even as low as 20%, the electromotive force relative to the change of the concentration of the gaseous carbon dioxide is reduced, failing to attain satisfactory detection and it can not be discriminated whether the change of the electromotive force is attributable to that of the concentration of the gaseous carbon dioxide or to that of the humidity.

In view of the above, although an improved method has been proposed, for example, of covering the detection electrode with such a gas permeable membrane that allows only the gaseous carbon dioxide but not water content to pass therethrough, preparation of the permeation membrane is extremely troublesome, as well as the effect is not sufficient and it has been difficult to dissolve the foregoing problem in this prior art.

OBJECT OF THE INVENTION

The object of the present invention is to overcome the foregoing problems in the prior art and provide a gaseous carbon dioxide detection sensor capable of measuring the concentration of gaseous carbon dioxide at a high accuracy by improving the humidity characteristic and the response characteristic of the gaseous carbon dioxide detection sensor using a solid electrolyte.

SUMMARY OF THE INVENTION

The foregoing object of the present invention can be attained by a gaseous carbon dioxide detection sensor comprising a detection electrode and a reference electrode opposed on both sides of an ionic conductor, wherein a mixture comprising one mol of an alkali metal carbonate and more than one mol of an alkaline earth metal carbonate is used as a detection material for the detection electrode.

A further excellent effect can be expected by using a solid solution comprising an alkali metal carbonate and an alkaline earth metal carbonate not containing crystals of the alkali metal carbonate as the detection material.

In the gaseous carbon dioxide detection sensor according to the present invention, the detection electrode is constituted with a mixture comprising one mol of an alkali metal carbonate and more than one mol of an alkaline earth metal carbonate, preferably, a solid-solution thereof not containing crystals of the alkali metal carbonate covered as the detection material on an electrode formed with a platinum gauge deposed with platinum black or the like. As the alkali metal carbonate constituting the detection material, lithium carbonate, sodium carbonate and potassium carbonate are used preferably alone or as a mixture of two or more of them. Further, as the alkaline earth metal carbonate, calcium carbonate, strontium carbonate and barium carbonate are preferably used alone or as a mixture of two or more of them.

The solid solution comprising the alkali metal carbonate and the alkaline earth metal carbonate does not contain crystals of the alkali metal carbonate. That is, since crystals of the alkali metal carbonate alone tend to be caused if the blending ratio of the alkaline earth metal carbonate to the alkali metal carbonate is small in the solid solution, a greater blending amount of the alkali metal carbonate is not desirable. On the other hand, if the blending amount of the alkali metal carbonate is small, it is preferred since the crystals of the alkali metal carbonate alone are less formed but this makes the melting point of the solid solution higher to make the working condition severer upon forming the detection electrode.

The blending ratio between the alkali metal carbonate and the alkaline earth metal carbonate is different depending on the kinds of the alkali metal carbonate and the alkaline earth metal carbonate to be combine and it is generally preferred to use a smaller amount of the alkali metal carbonate and a greater amount of the alkaline earth metal carbonate in combination.

As the solid electrolyte, sintering material such as β-alumina or NASICON, as well as other appropriate sodium ion conductors may be used with no particular restriction only thereto. For the reference electrode, a platinum gauge deposited with platinum black or a vapor deposited platinum film may be used, for example and it may be covered, depending on the case, with a mixture, for example, of an alkali metal carbonate and an alkaline earth metal carbonate like that the detection electrode. It is necessary for such a reference electrode that it is covered with a gas impermeable cover so as to be free from the effect of the concentration of the gaseous carbon dioxide in a gas to be detected.

In the gaseous carbon dioxide detection sensor having thus been constituted as described above, when a gas to be detected is in contact with the detection electrode in a state heated to about 400° C. to 600°, since an electromotive force corresponding to the partial pressure of the gaseous carbon dioxide in the gas to be detected is caused to the detection electrode, the concentration of the gaseous carbon dioxide in the gas to be detected can be detected, free from the effect of the humidity, by measuring the electromotive force between the detection electrode and the reference electrode.

DESCRIPTION OF THE ACCOMPANYING DRAWINGS

These and other objects, as well as advantageous features of the present invention will become apparent by reading the following descriptions with respect to the preferred embodiments according to the present invention referring to the accompanying drawings, wherein FIG. 1 is a view illustrating the structure of a gaseous carbon dioxide detection sensor according to the present invention;

DESCRIPTION OF PREFERRED EMBODIMENTS

The preferred embodiments of the present invention will be described with reference to the drawings.

Figure 1:
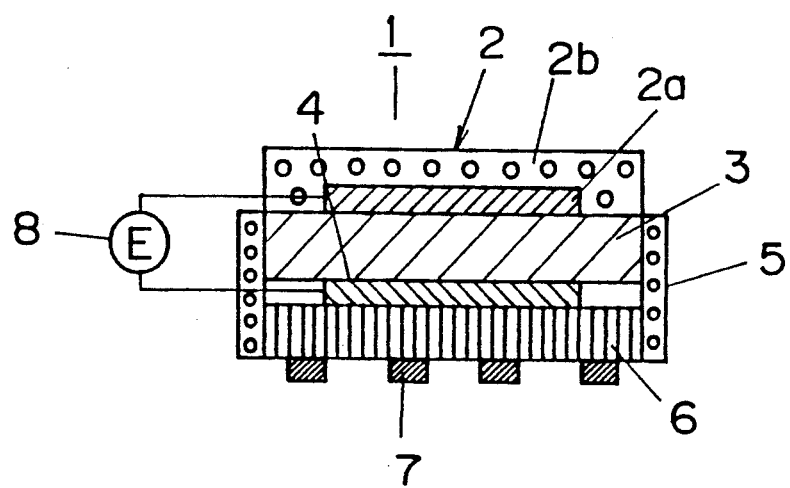

FIG. 1 shows a structure of a gaseous carbon dioxide detection sensor according to the present invention. In the figure, are shown a gaseous carbon dioxide detection sensor 1 and a detection electrode 2. The detection electrode 2 comprises an electrode 2a, for example, made of a platinum gauge deposited with platinum black and a detection material layer 2b comprising a mixture of an alkali metal carbonate and an alkali earth metal carbonate and covered on the electrode 2a.

There are also shown an ionic conductor 3 and a reference electrode 4 formed, for example, with a platinum gauge deposited with platinum black and sealed by applying a cover 5 made of glass for shielding from a gas to be detected. A heater 7 made of a platinum layer is disposed at the back of a ceramic substrate 6.

Figure 2:
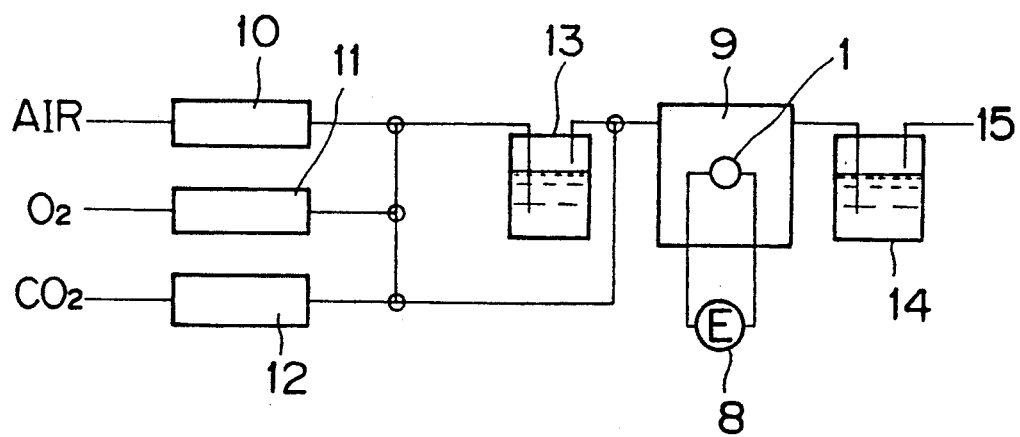
FIG. 2 is a view showing a structure of a device for measuring the electromotive force characteristic of the gaseous carbon dioxide detection sensor relative to gaseous carbon dioxide.
Figure 3:
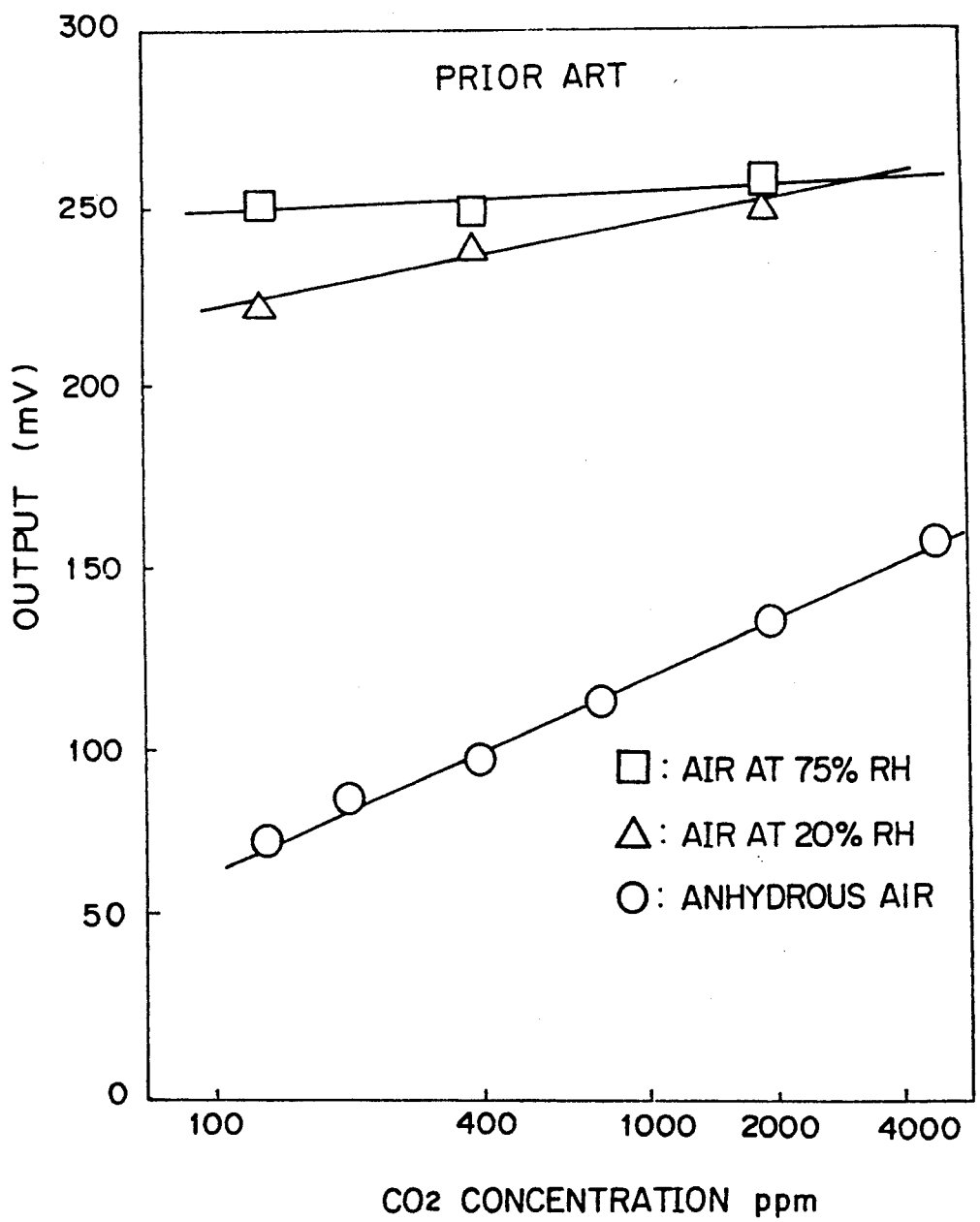
FIG. 3 is a characteristic graph for the detection of gaseous carbon dioxide in humid air and anhydrous air for a gaseous carbon dioxide detection sensor in the prior art.

The gaseous carbon dioxide detection sensor 1 is disposed in a chamber 9 of a measuring device shown in FIG. 2 and heated by the heater 7. Air, $O_2$ and gaseous carbon dioxide are mixed through flow meters 10, 11 and 12 respectively to a predetermined concentration and supplied to the chamber 9, and an electromotive force between the detection electrode 2 and the reference electrode 5 is measured by a volt meter 8. In the figure, are shown a water vessel 13 for adding a moisture content to the gas to be measured, a back flow preventive trap 14 and an exhaust opening 15.

FIRST EMBODIMENT

This embodiment uses NASICON as the sodium ionic conductor 3, and sodium carbonate and barium carbonate solid-solubilized at a molar ratio of 1:1.7 is used as a mixture of the alkali metal carbonate and the alkaline earth metal carbonate of the detection material layer 2b for covering the electrode 2a formed with a platinum gauge deposited with platinum black. Other constitutions are the same as described above.

Figure 4:
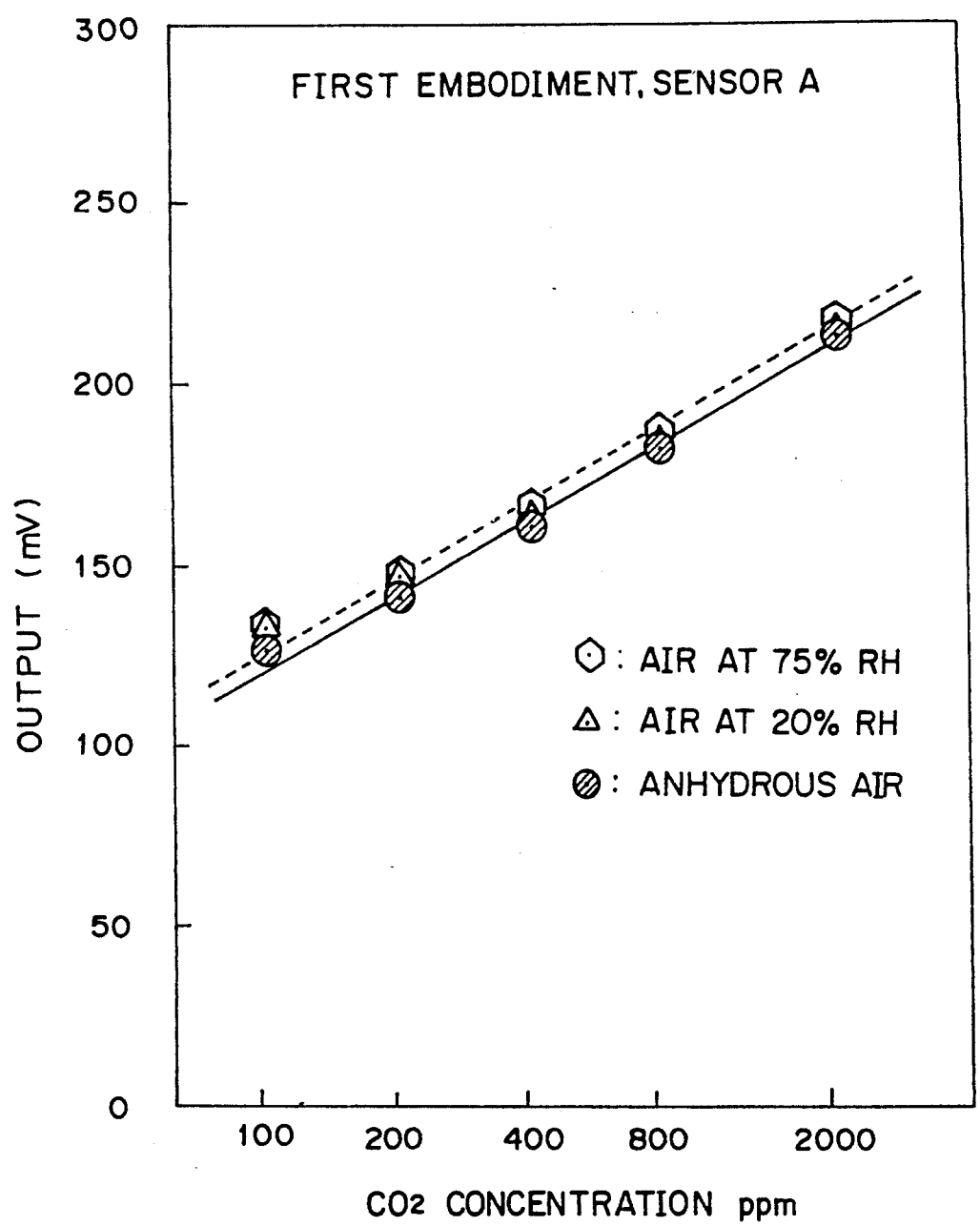
FIG. 4 is a characteristic graph for the detection of gaseous carbon dioxide in humid air and anhydrous air for a gaseous carbon dioxide detection sensor A of a first embodiment according to the present invention.

The gaseous carbon dioxide detection sensor A of the first embodiment according to the present invention is heated by the heater to a element temperature of 550° C. in the measuring device shown in FIG. 2, and the characteristic of the electromotive force relative to gaseous carbon dioxide at a concentration of 100 to 2000 ppm was measured in a humid air and an anhydrous air. The results are shown in FIG. 4. As can be seen from the figure, the sensor shows substantially the same characteristics in the humid air at 20% and 75% humidity, as well as in the anhydrous air.

FIRST COMPARATIVE EMBODIMENT

Figure 5:
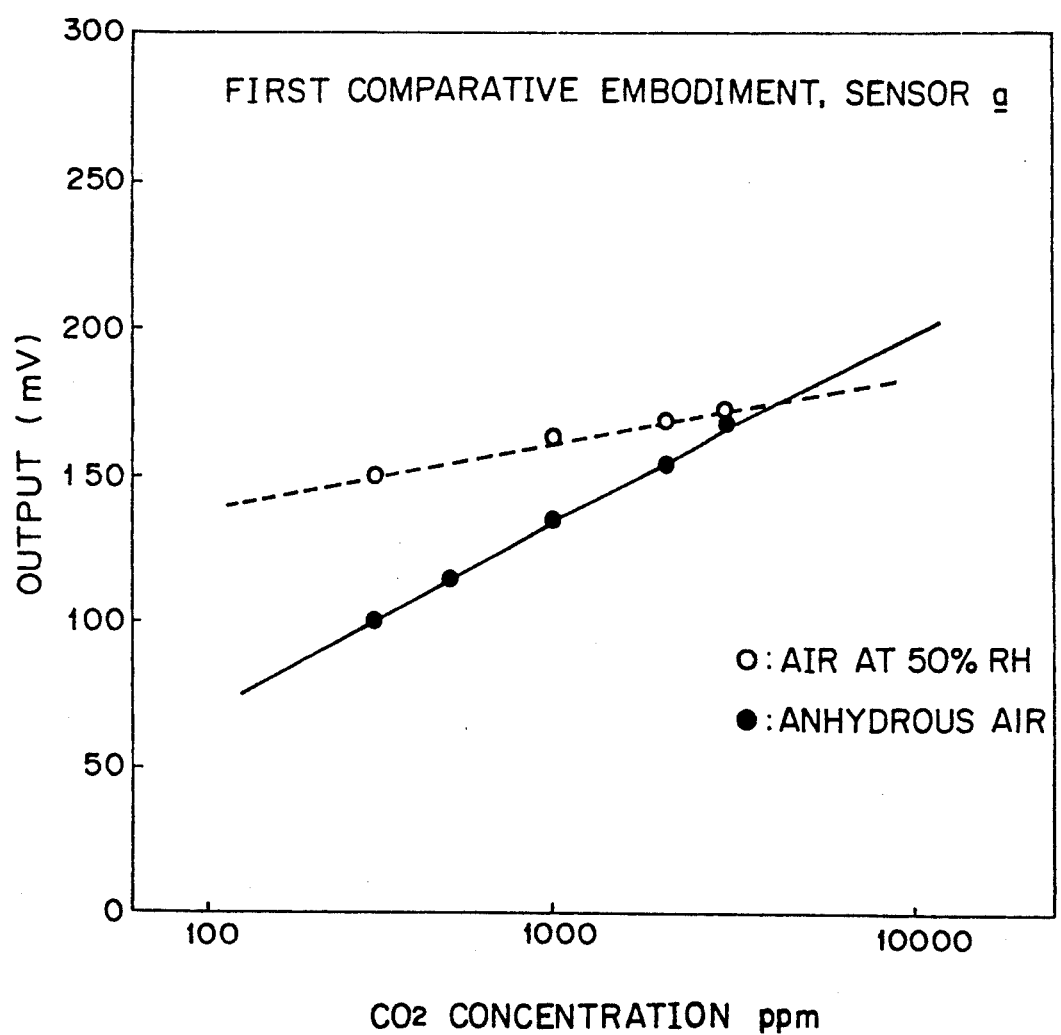
FIG. 5 is a characteristic graph for the detection of gaseous carbon dioxide in humid air and anhydrous air for a gaseous carbon dioxide detection sensor a of a first comparative embodiment.

Using a gaseous carbon dioxide detection sensor a constituted quite in the same manner as in the first embodiment except for using, as the detection material, a solid solution comprising sodium carbonate and barium carbonate at a molar ratio of 1:1 instead of 1:1.7 in the first embodiment, the characteristic of the electromotive force relative to gaseous carbon dioxide was measured in a humid air at 50% humidity and in an anhydrous air in the same manner as in the first embodiment. The results are shown in FIG. 5. As can be seen from the figure, the output from the gaseous carbon dioxide detection sensor a of the first comparative embodiment changes greatly depending on the moisture content in the gas to be detected.

FIRST REFERENCE EMBODIMENT

Figure 14:
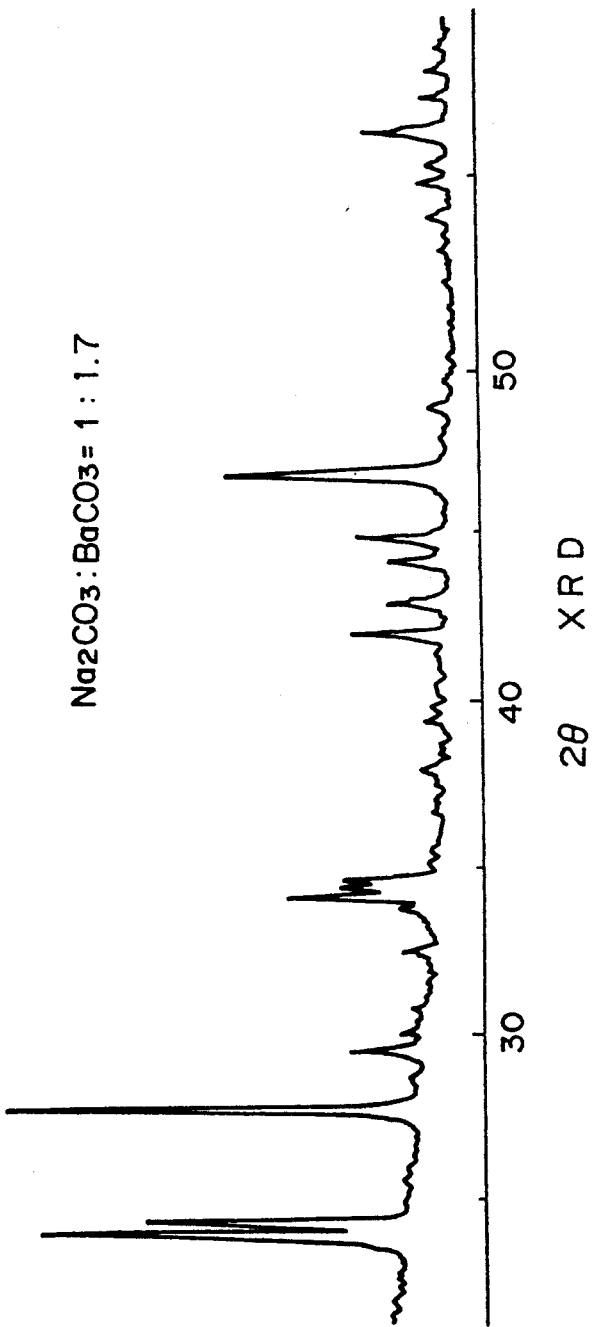
FIG. 14 is an X-ray diffraction chart for a solid solution of sodium carbonate and barium carbonate at 1:1.7 molar ratio.
Figure 15:
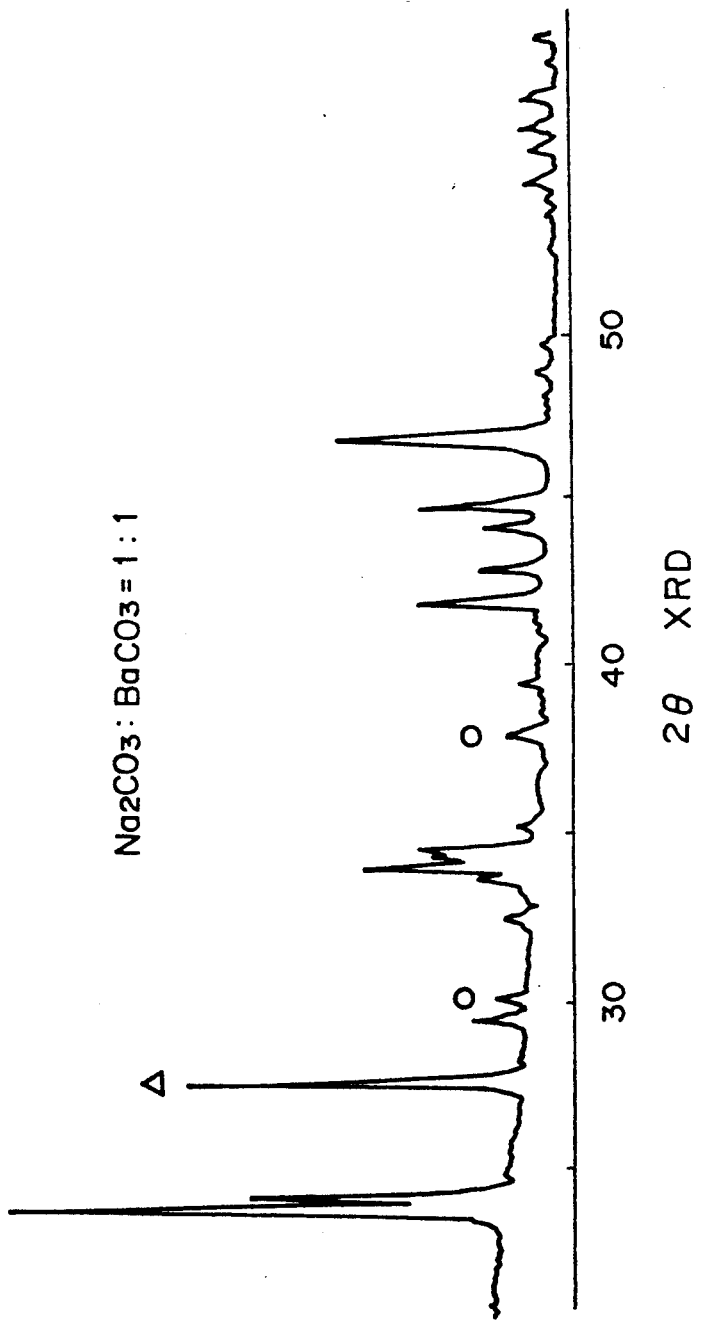
FIG. 15 is an X-ray diffraction chart for a solid solution of sodium carbonate and barium carbonate at 1:1 molar ratio.
Figure 24:
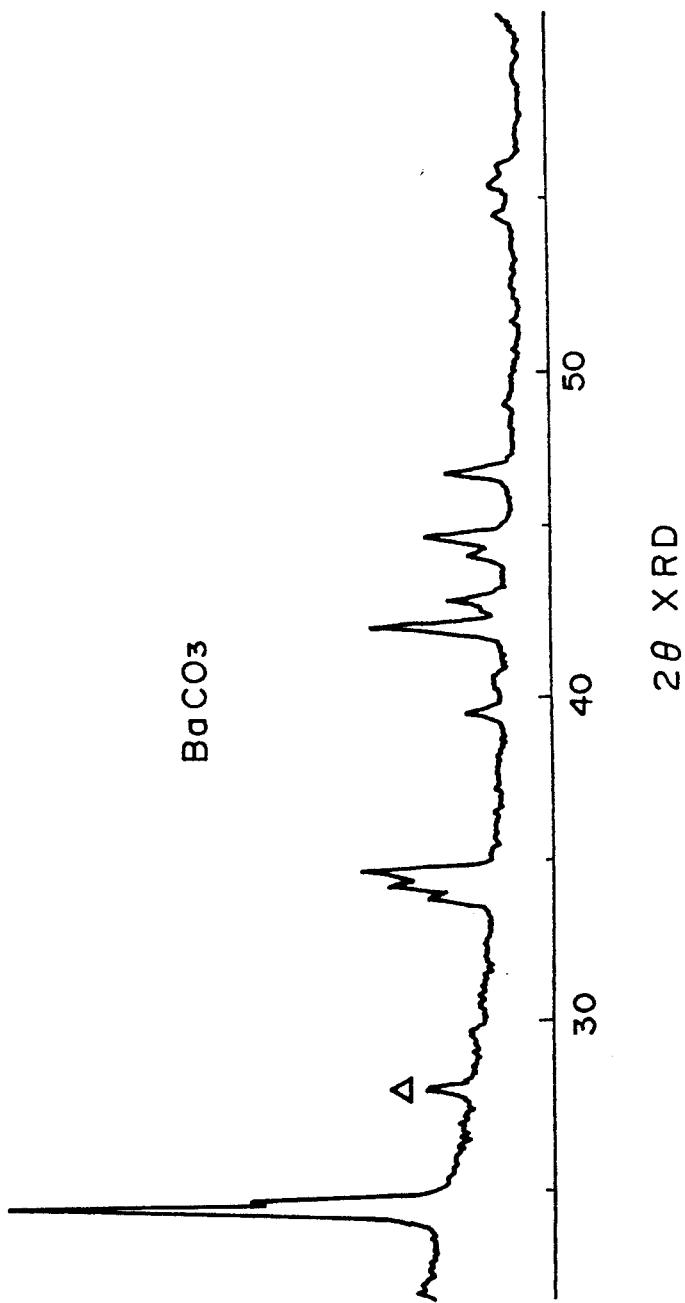
FIG. 24 is an X-ray refraction chart for barium carbonate.
Figure 27:
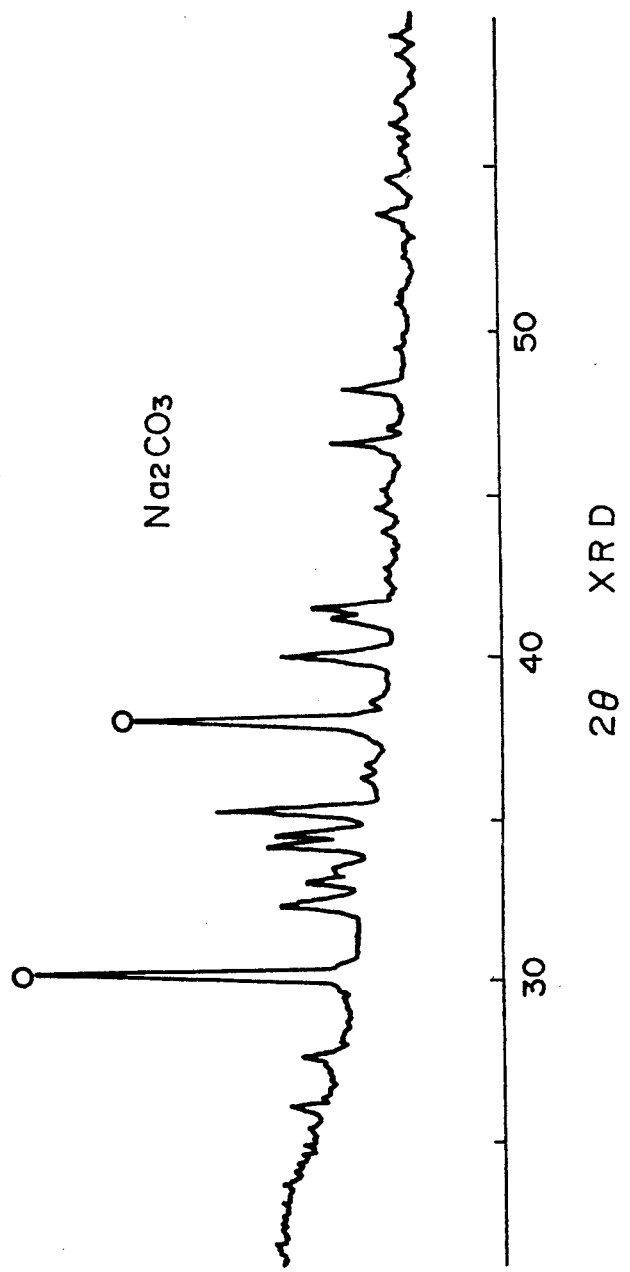
FIG. 27 is an X-ray refraction chart for sodium carbonate.

Crystal structures were analyzed by X-ray diffractiometry for the solid solution comprising sodium carbonate and barium carbonate at a 1:1.7 molar ratio used in the first embodiment and the solid solution at a 1:1 molar ratio used in the first comparative embodiment. The charts are shown in FIG. 14 and FIG. 15. In comparison with the chart for barium carbonate in FIG. 24 and the chart for sodium carbonate in FIG. 27 for the reference, it can be seen that the solid solution at the 1:1 molar ratio shows peaks inherent to the crystals of sodium carbonate, whereas the solid solution at the 1:1.7 molar ratio shows no such peaks and does not contain the crystals of sodium carbonate.

SECOND EMBODIMENT

This embodiment provides a gaseous carbon dioxide detection sensor constituted quite in the same manner as in the first embodiment except for using, as the detection material, a solid solution comprising lithium carbonate and barium carbonate at a 1:2.5 molar ratio instead of using the solid solution comprising sodium carbonate and barium carbonate at a 1:1.7 molar ratio.

Figure 6:
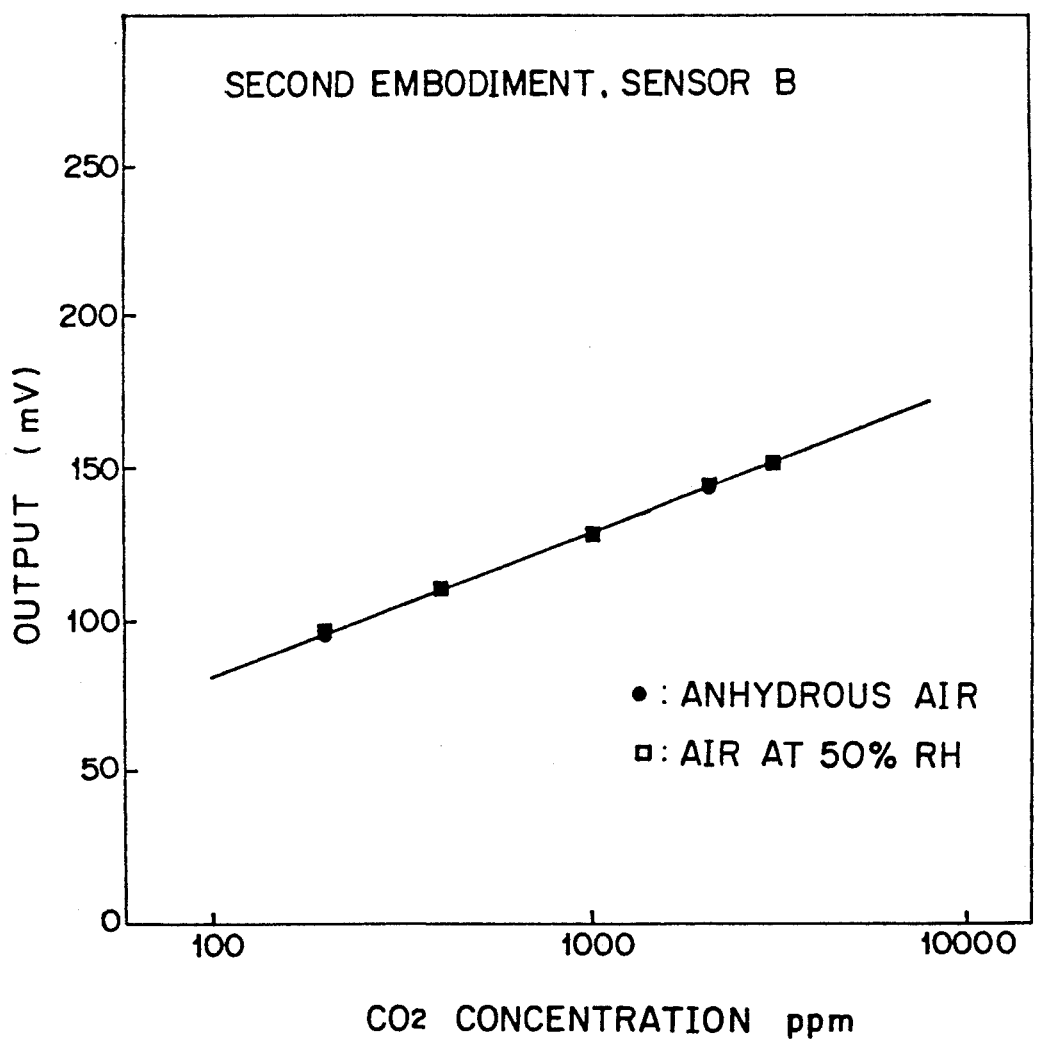
FIG. 6 is a characteristic graph for the detection of gaseous carbon dioxide in humid air and anhydrous air for a gaseous carbon dioxide detection sensor B of a second embodiment according to the present invention.

The gaseous carbon dioxide detection sensor B of the second embodiment according to the present invention was heated to an element temperature of 550° C. like that in the first embodiment and the characteristic of the electromotive force relative to gaseous carbon dioxide was measured in a humid air at 50% humidity and in an anhydrous air. As can be seen from the results shown in FIG. 6, the sensor shows substantially the same characteristic in the humid air as well as in the anhydrous air.

SECOND COMPARATIVE EMBODIMENT

Figure 7:
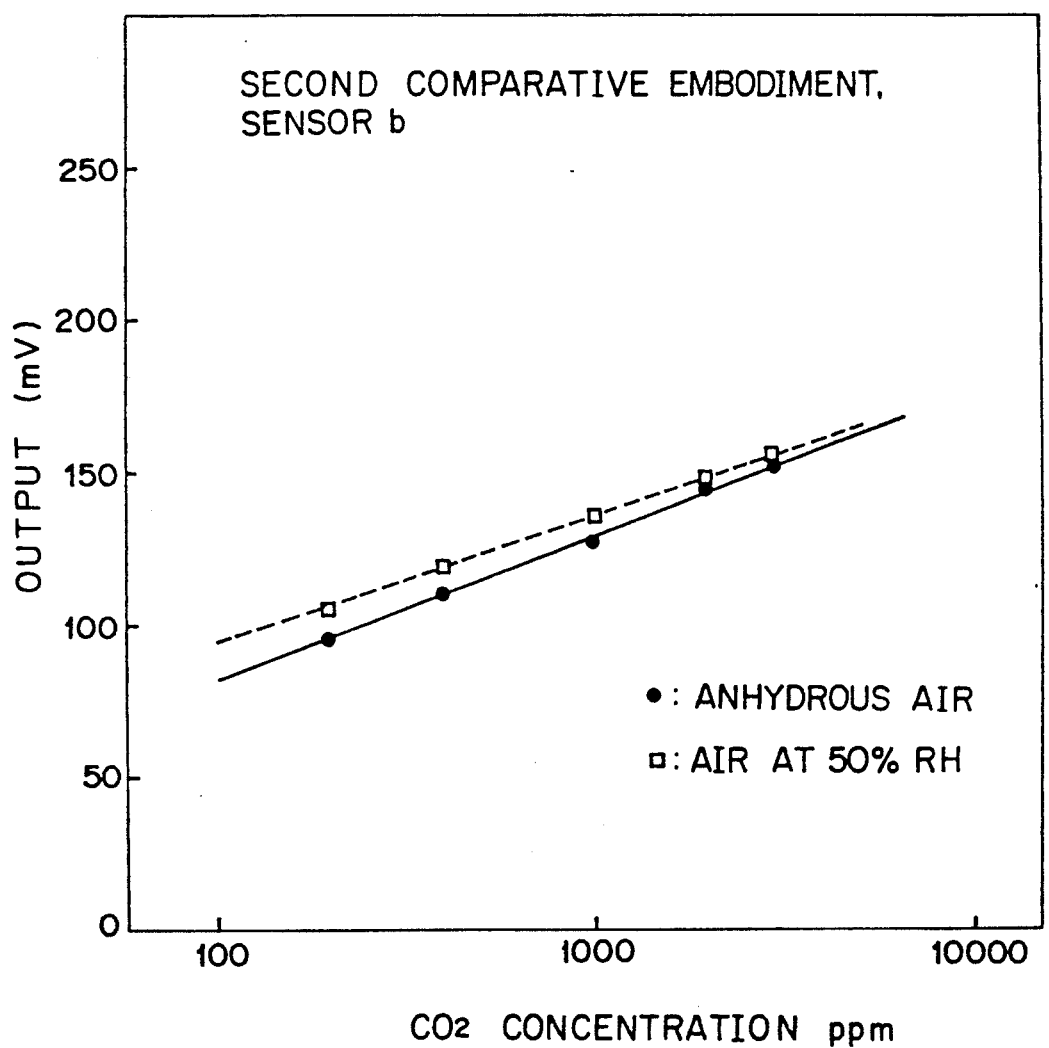
FIG. 7 is a characteristic graph for the detection of gaseous carbon dioxide in humid air and anhydrous air for a gaseous carbon dioxide detection sensor b of a second comparative embodiment.

Using a gaseous carbon dioxide detection sensor b constituted quite in the same manner as in the second embodiment except for using, as the detection material, a solid solution comprising lithium carbonate and barium carbonate at a molar ratio of 1:1 instead of 1:2.5, the characteristic of the electromotive force relative to gaseous carbon dioxide was measured in a humid air at 50% humidity and an anhydrous air in the same manner as in the second embodiment. As can be seen from the results shown in FIG. 7, the output from the gaseous carbon dioxide detection sensor b of the second comparative embodiment changes greatly depending on the moisture content in the gas to be detected.

SECOND REFERENCE EMBODIMENT

Figure 16:
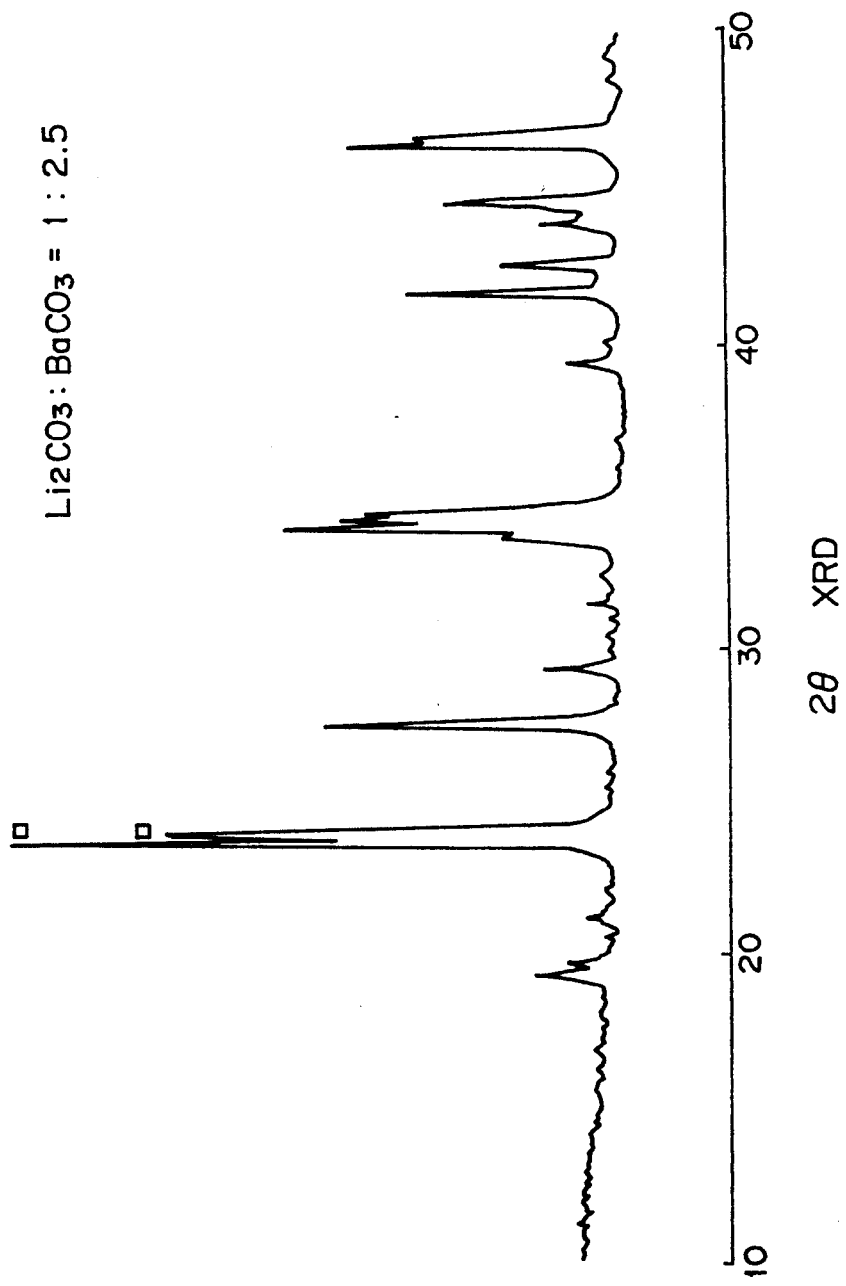
FIG. 16 is an X-ray diffraction chart for a solid solution of lithium carbonate and barium carbonate at 1:2.5 molar ratio.
Figure 17:
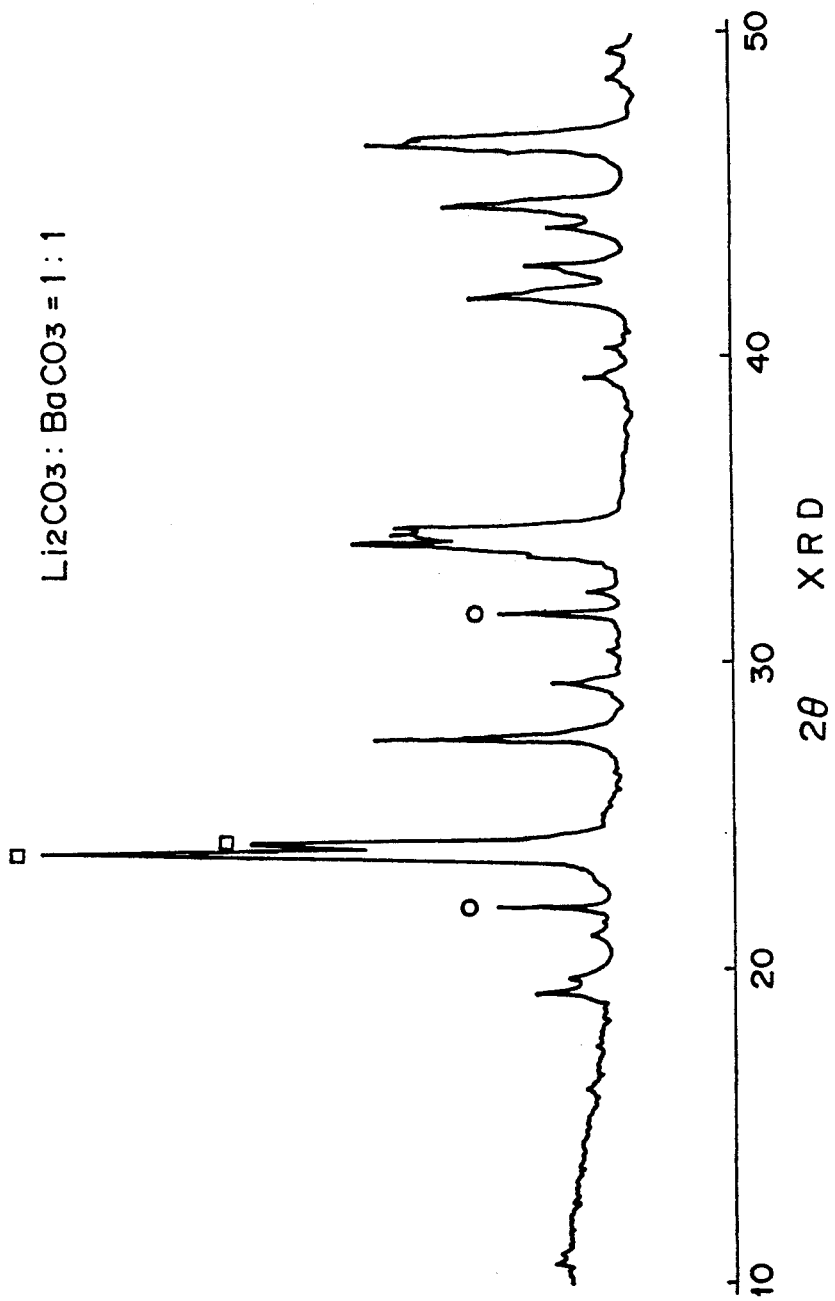
FIG. 17 is an X-ray diffraction chart for a solid solution of lithium carbonate and barium carbonate at 1:1 molar ratio.
Figure 28:
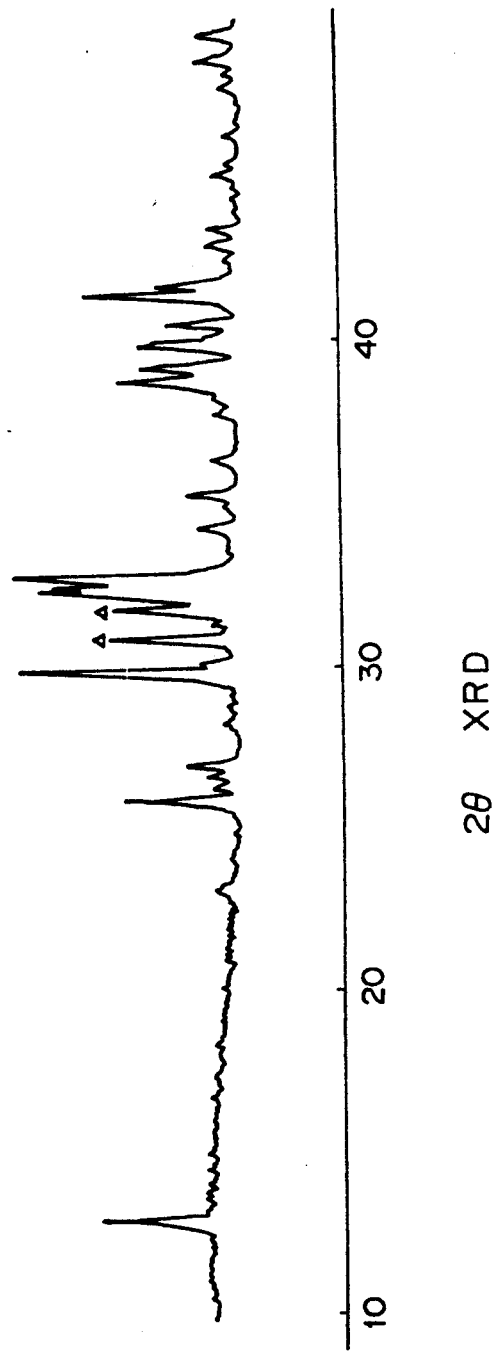
FIG. 28 is an X-ray refraction chart for lithium carbonate.

Crystal structures were analyzed by X-ray diffractiometry for the solid solution comprising lithium carbonate and barium carbonate at a 1:2.5 molar ratio used in the second embodiment and the solid solution at a 1:1 molar ratio used in the first comparative embodiment. The charts are shown in FIG. 16 and FIG. 17. In comparison with a chart for barium carbonate in FIG. 24 and a chart for sodium carbonate in FIG. 28 for the reference, it can be seen that the solid solution at the 1:1 molar ratio shows peaks inherent to the crystals of lithium carbonate, whereas the solid solution at the 1:2.5 molar ratio shows no such peaks and does not contain the crystals of lithium carbonate.

THIRD EMBODIMENT

This embodiment provides a gaseous carbon dioxide detection sensor constituted quite in the same manner as in the first embodiment except for using, as the detection material, a solid solution comprising potassium carbonate and barium carbonate at a 1:3 molar ratio instead of using the solid solution comprising sodium carbonate and barium carbonate at a 1:1.7 molar ratio.

Figure 8:
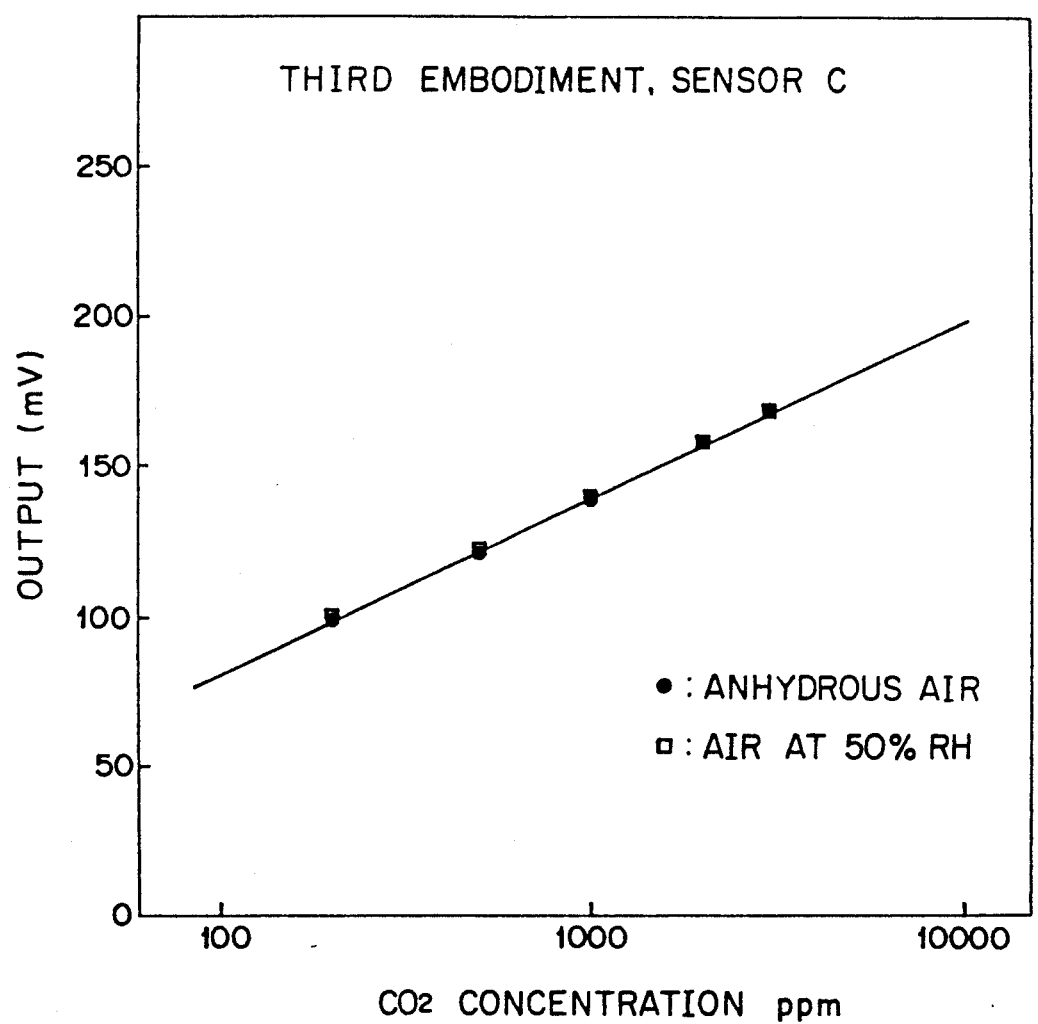
FIG. 8 is a characteristic graph for the detection of gaseous carbon dioxide in humid air and anhydrous air for a gaseous carbon dioxide detection sensor C of a third embodiment according to the present invention.

The gaseous carbon dioxide detection sensor C of the third embodiment according to the present invention was heated to an element temperature of 550° C. like that in the second embodiment and the characteristic of the electromotive force relative to gaseous carbon dioxide was measured in a humid air and in an anhydrous air. As can be seen from the results shown in FIG. 8, the sensor shows substantially the same characteristics in the humid air as well as in the anhydrous air.

THIRD COMPARATIVE EMBODIMENT

Figure 9:
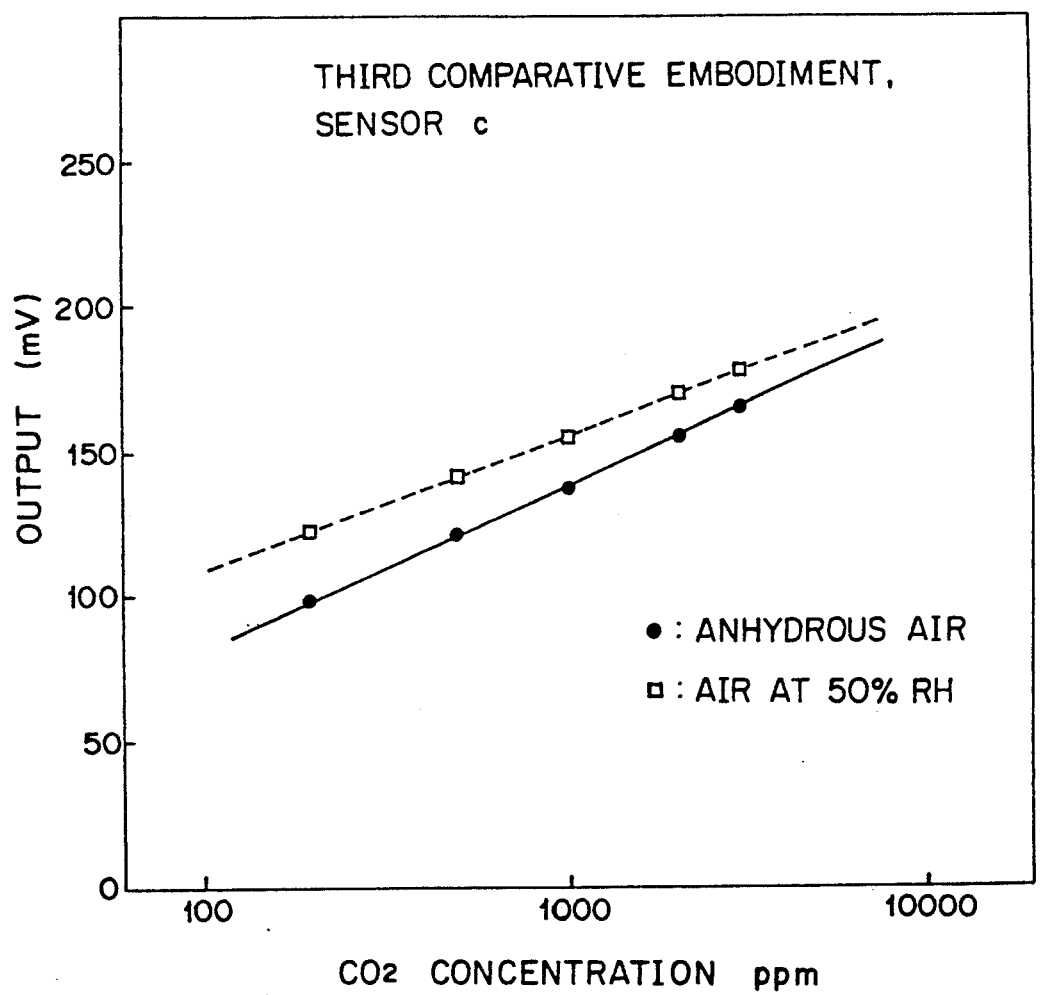
FIG. 9 is a characteristic graph for the detection of gaseous carbon dioxide in humid air and anhydrous air for a gaseous carbon dioxide detection sensor c of a third comparative embodiment.

Using a gaseous carbon dioxide detection sensor c constituted quite in the same manner as in the third embodiment except for using, as the detection material, a solid solution comprising potassium carbonate and barium carbonate at a molar ratio of 1:1 instead of 1:3, the characteristic of the electromotive force relative to gaseous carbon dioxide was measured to in a humid air and in an anhydrous air in the same manner as in the embodiment. As can be seen from the results shown in FIG. 9, the output from the gaseous carbon dioxide detection sensor c of the third comparative embodiment changes greatly depending on the moisture content in the gas to be detected.

THIRD REFERENCE EMBODIMENT

Figure 18:
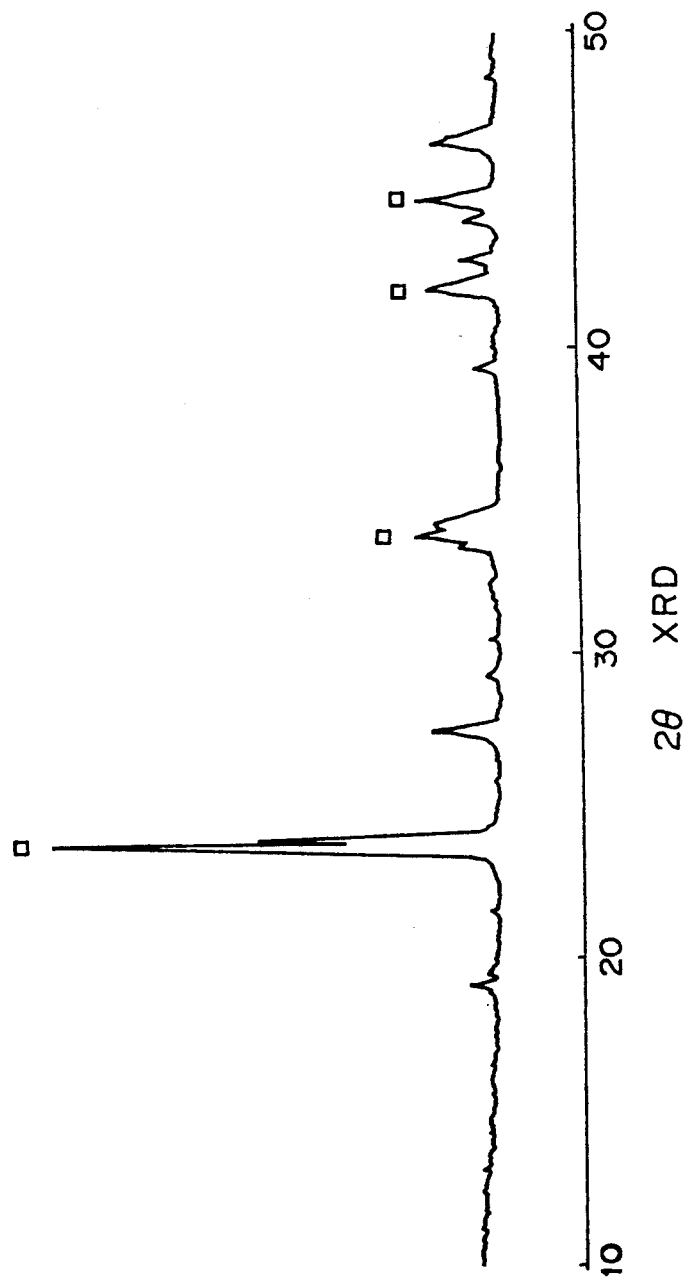
FIG. 18 is an X-ray diffraction chart for a solid solution of potassium carbonate and barium carbonate at 1:3 molar ratio.
Figure 19:
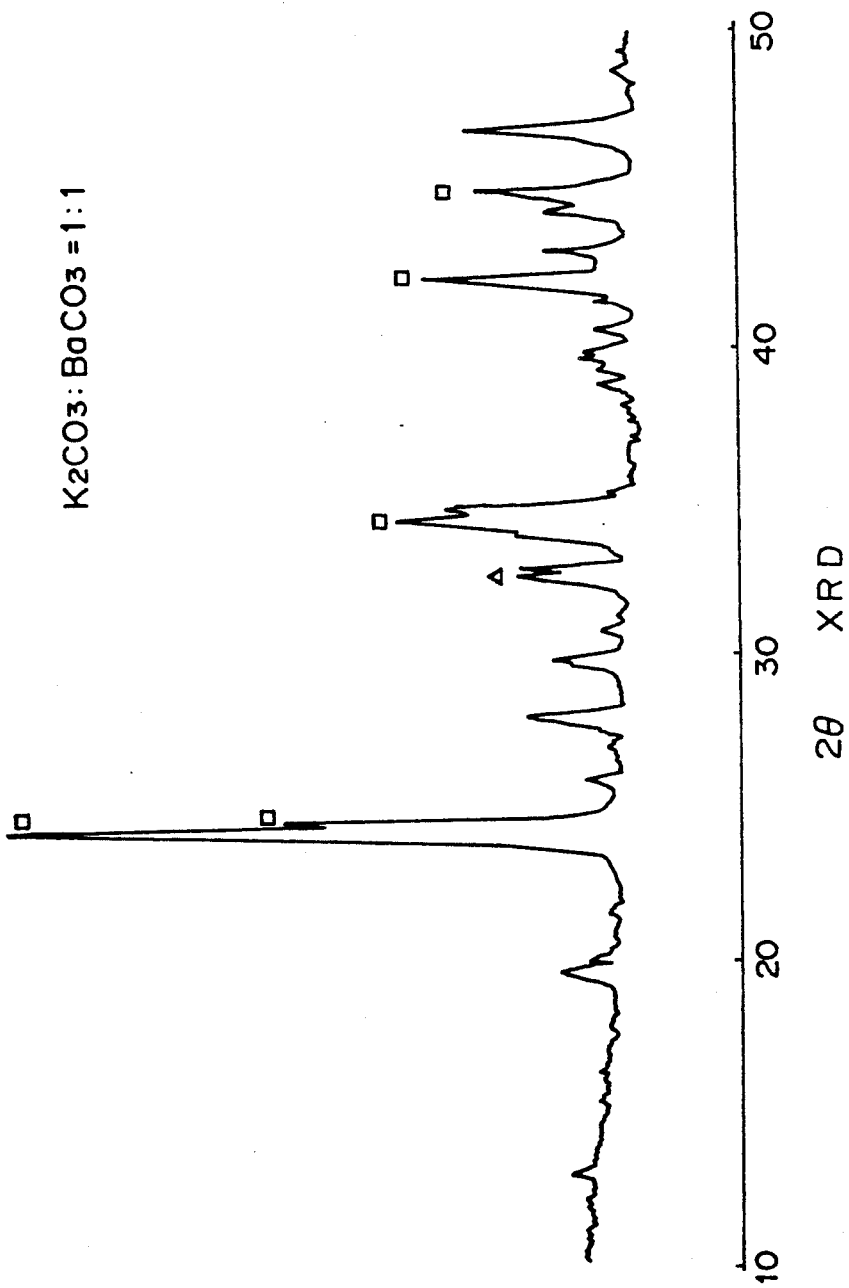
FIG. 19 is an X-ray diffraction chart for a solid solution of potassium carbonate and barium carbonate at 1:1 molar ratio.
Figure 29:
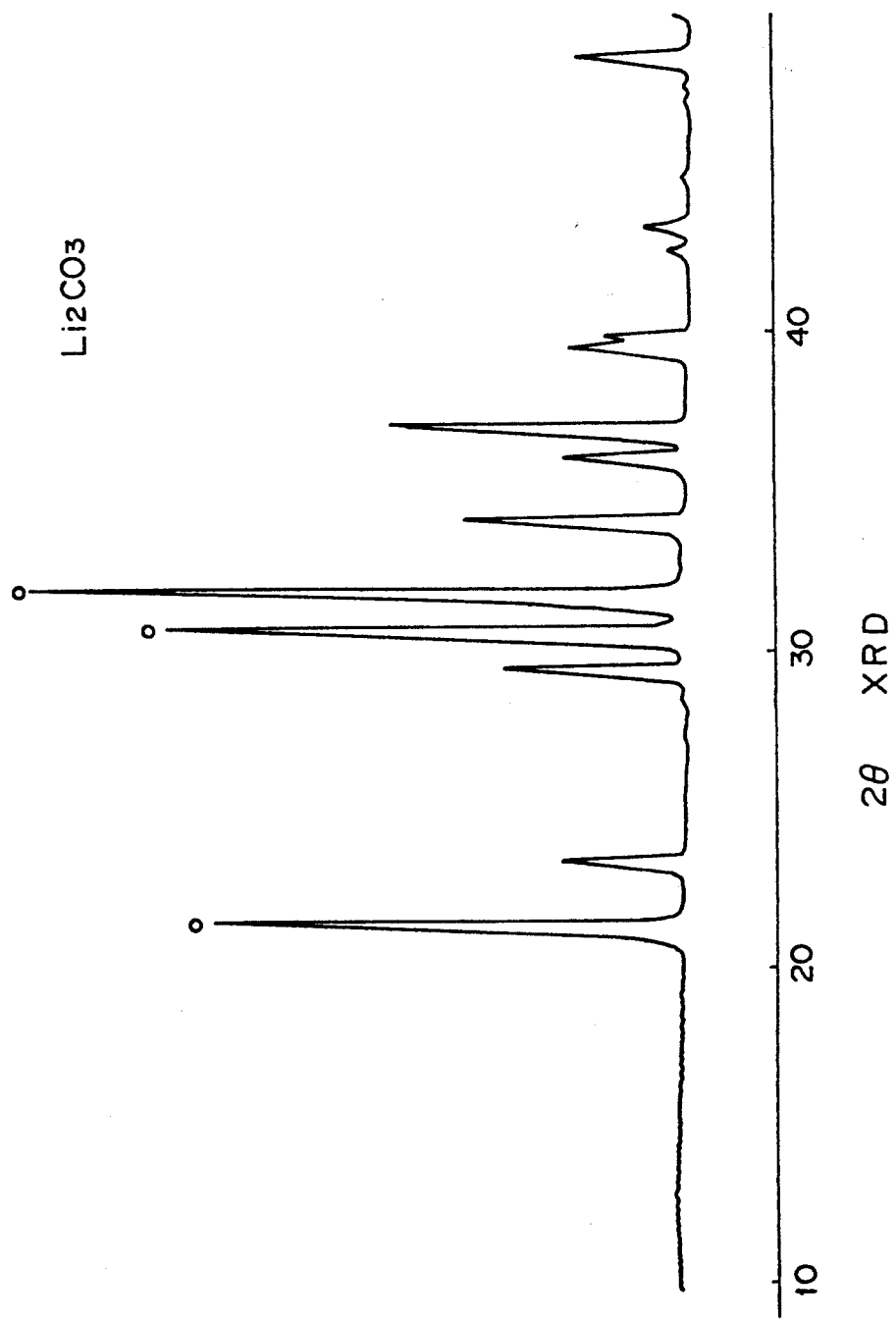
FIG. 29 is an X-ray refraction chart for potassium carbonate.

Crystal structures were analyzed by X-ray diffractiometry for the solid solution comprising potassium carbonate and barium carbonate at a 1:3 molar ratio used in the third embodiment and the solid solution at a 1:1 molar ratio used in the first comparative embodiment. The charts are shown in FIG. 18 and FIG. 19. In comparison with a chart for barium carbonate in FIG. 24 and a chart for sodium carbonate in FIG. 29 for the reference, it can be seen that the solid solution at the 1:1 molar ratio shows peaks inherent to the crystals of potassium carbonate, whereas the solid solution at the 1:3 molar ratio shows no such peaks and does not contain the crystals of potassium carbonate.

FOURTH EMBODIMENT

This embodiment provides a gaseous carbon dioxide detection sensor constituted quite in the same manner as in the first embodiment except for using, as the detection material, a solid solution comprising sodium carbonate and strontium carbonate at a 1:2 molar ratio instead of using the solid solution comprising sodium carbonate and barium carbonate at a 1:1.7 molar ratio.

Figure 10:
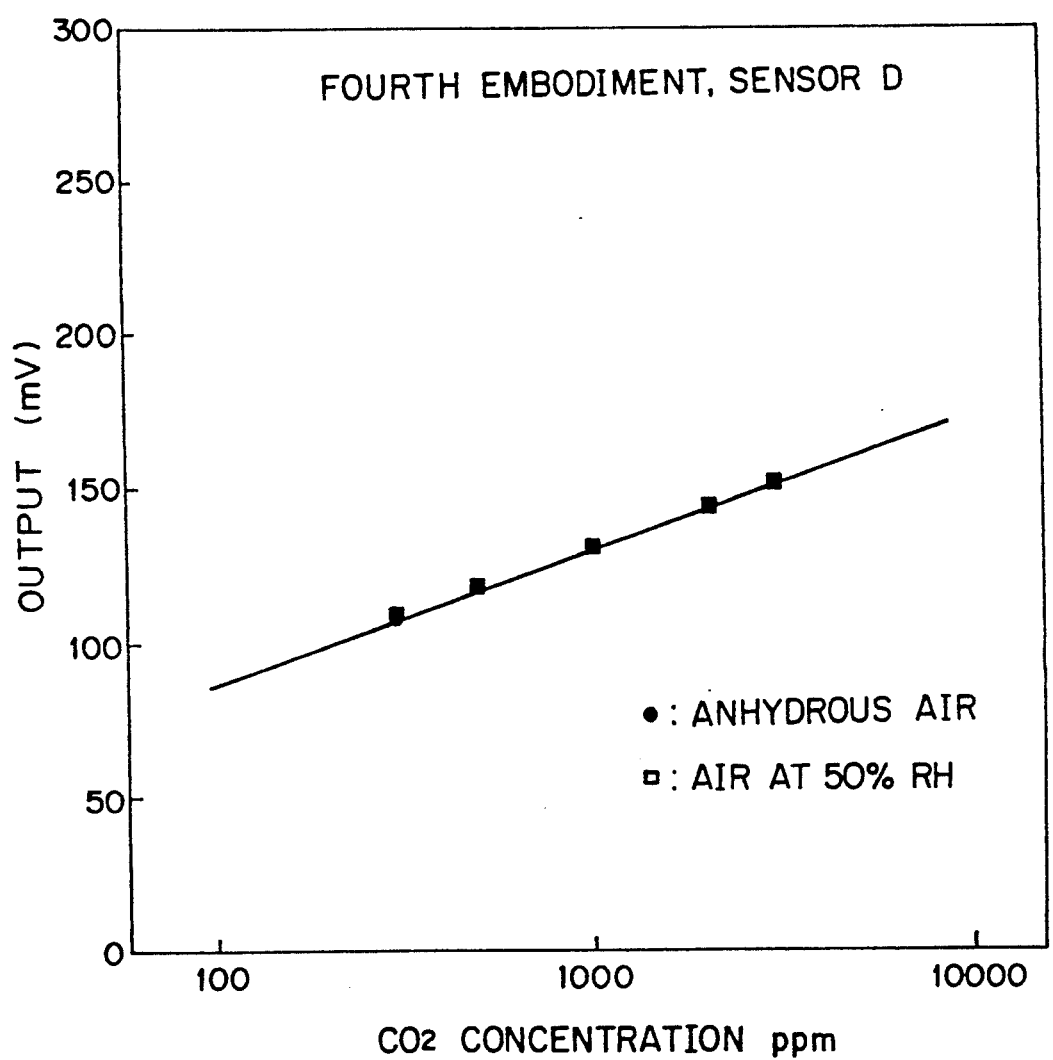
FIG. 10 is a characteristic graph for the detection of gaseous carbon dioxide in humid air and anhydrous air for a gaseous carbon dioxide detection sensor D of a fourth embodiment according to the present invention.

The gaseous carbon dioxide detection sensor D of the fourth embodiment according to the present invention was heated to an element temperature of 550° C. like that in the second embodiment and the characteristic of the electromotive force relative to gaseous carbon dioxide was measured in a humid air and in an anhydrous air. As can be seen from the results shown in FIG. 10, the sensor shows substantially the same characteristics in the humid air as well as in the anhydrous air.

FOURTH COMPARATIVE EMBODIMENT

Figure 11:
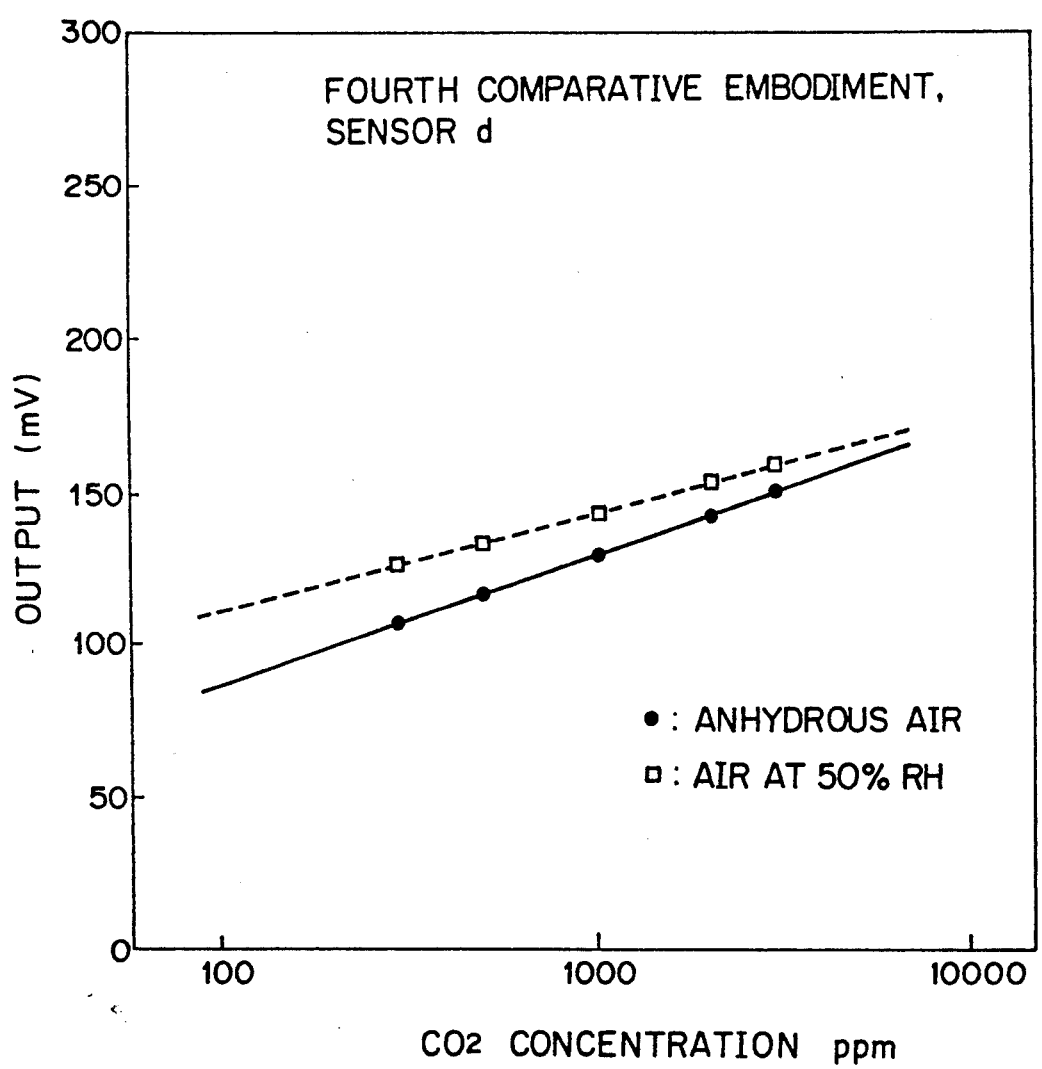
FIG. 11 is a characteristic graph for the detection of gaseous carbon dioxide in humid air and anhydrous air for a gaseous carbon dioxide detection sensor d of a fourth comparative embodiment.

Using a gaseous carbon dioxide detection sensor d constituted quite in the same manner as in the fourth embodiment except for using, as the detection material, a solid solution comprising sodium carbonate and strontium carbonate at a molar ratio of 1:1 instead of 1:2, the characteristic of the electromotive force relative to gaseous carbon dioxide was measured in a humid air and in an anhydrous air in the same manner as in the second embodiment. As can be seen from the results shown in FIG. 11, the output from the gaseous carbon dioxide detection sensor d of the fourth comparative embodiment changes greatly depending on the moisture content in the gas to be detected.

FOURTH REFERENCE EMBODIMENT

Figure 20:
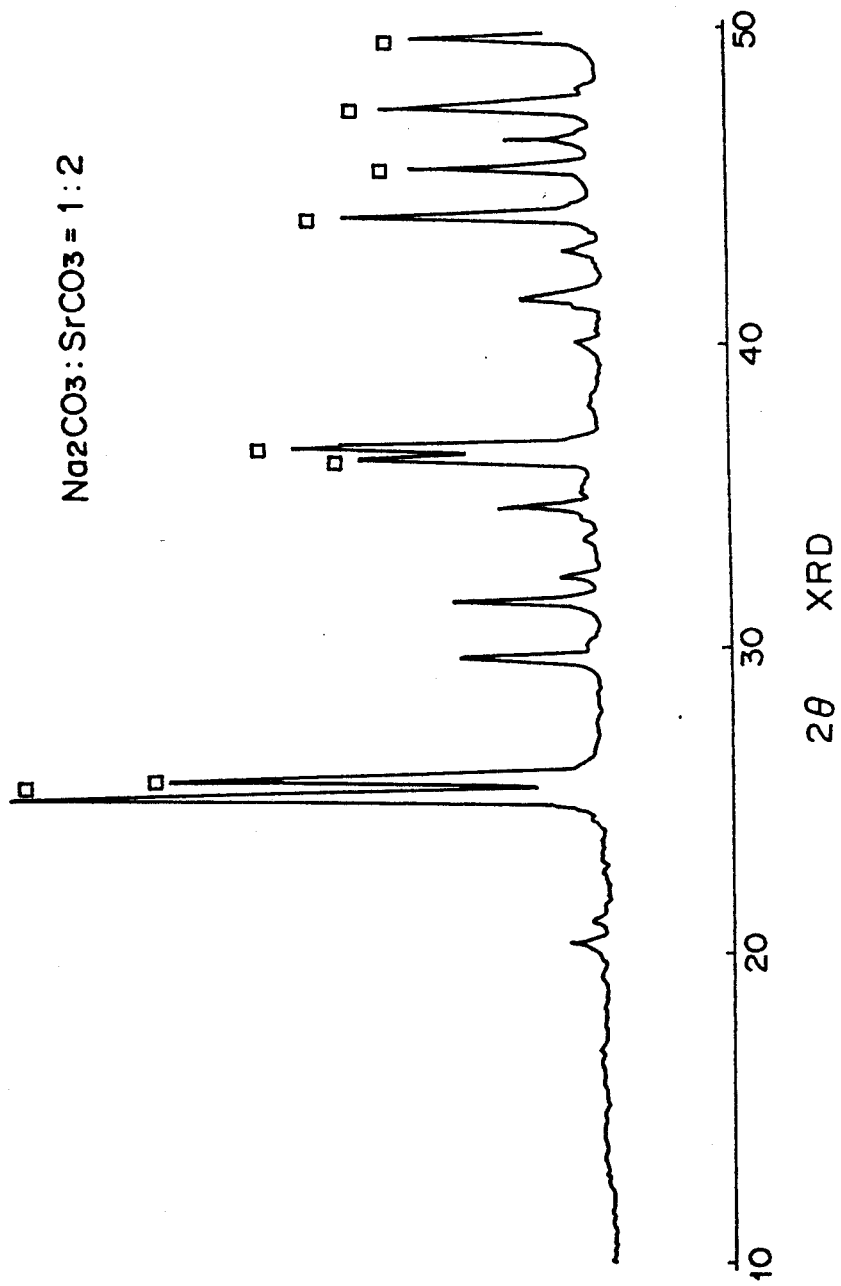
FIG. 20 is an X-ray diffraction chart for a solid solution of sodium carbonate and strontium carbonate at 1:2 molar ratio.
Figure 21:
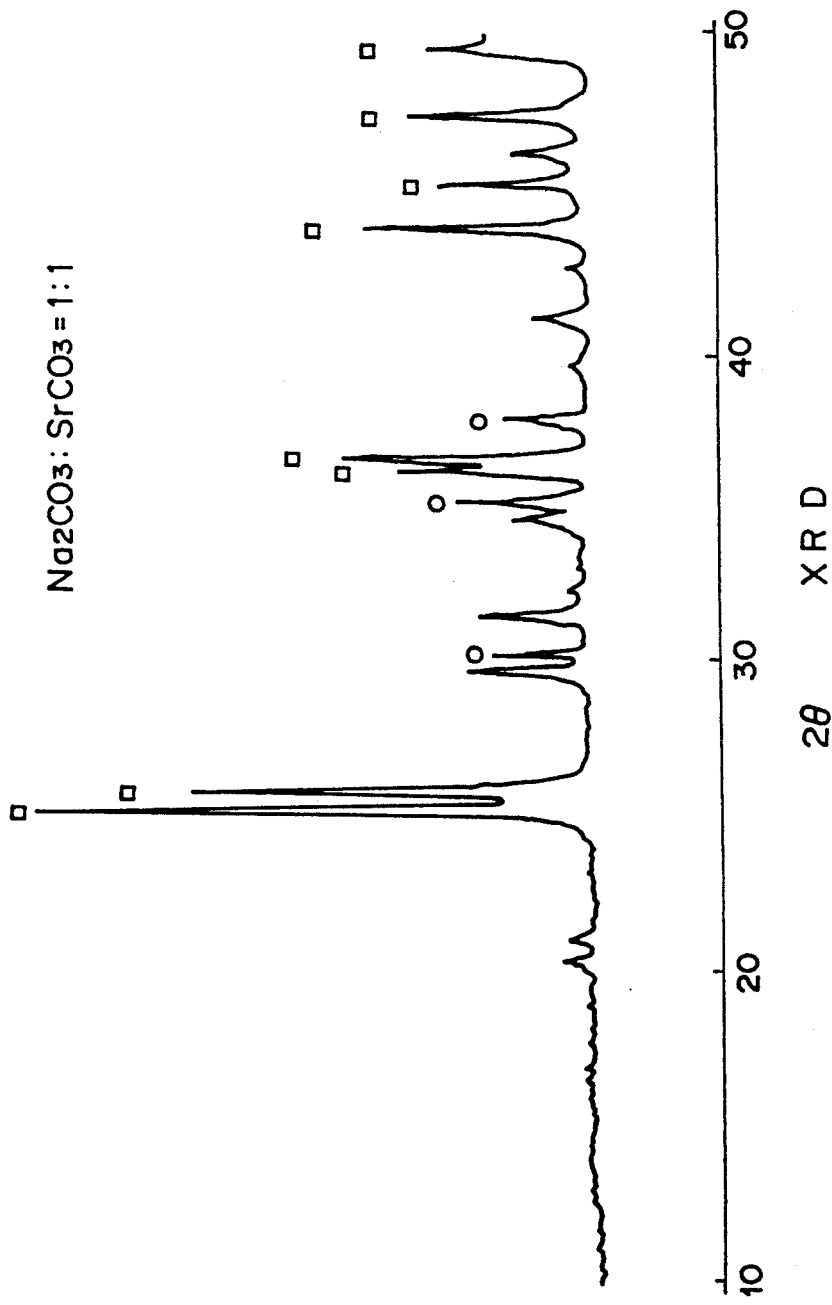
FIG. 21 is an X-ray diffraction chart for a solid solution of sodium carbonate and strontium carbonate at 1:1 molar ratio.
Figure 25:
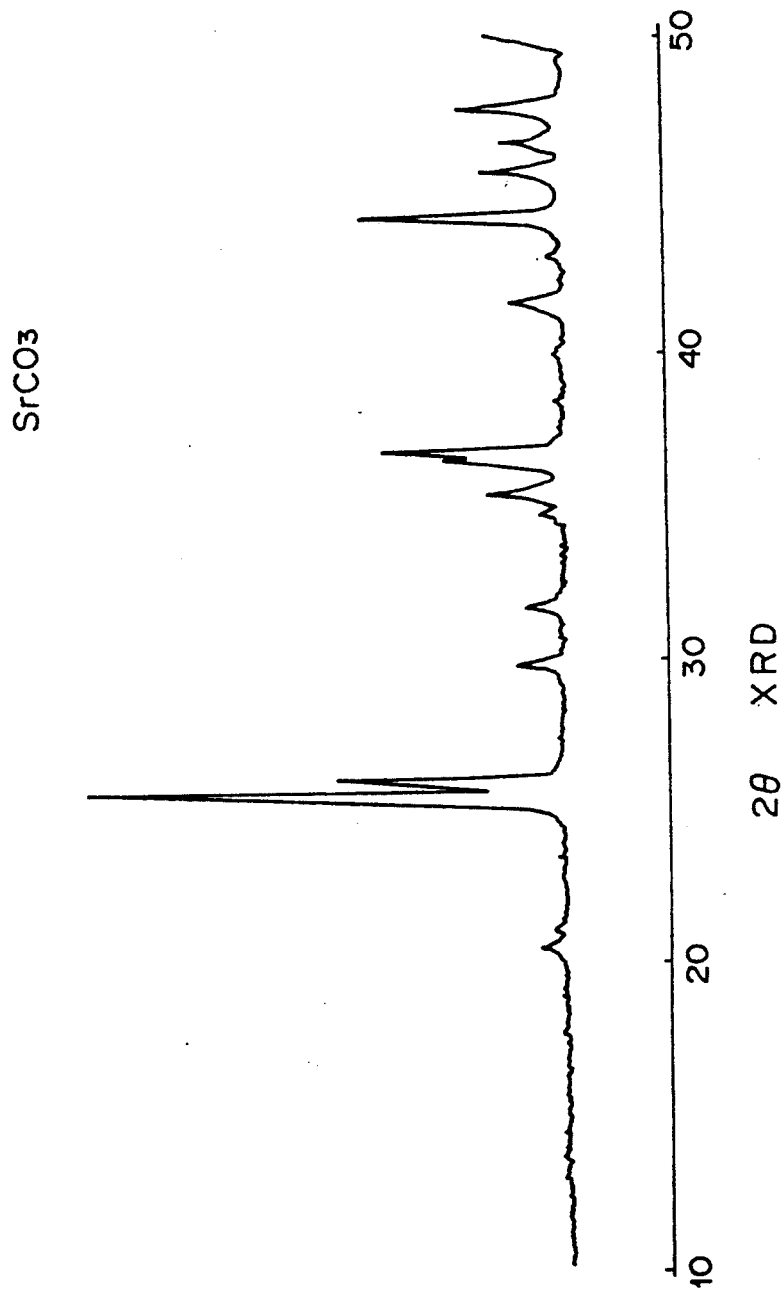
FIG. 25 is an X-ray refraction chart for strontium carbonate.

Crystal structures were analyzed by X-ray diffractiometry for the solid solution comprising sodium carbonate and strontium carbonate at a 1:2 molar ratio used in the fourth embodiment and the solid solution at a 1:1 molar ratio used in the fourth comparative embodiment. The charts are shown in FIG. 20 and FIG. 21. In comparison with a chart for strontium carbonate in FIG. 25 and a chart for sodium carbonate in FIG. 27 for the reference, it can be seen that the solid solution at the 1:1 molar ratio shows peaks inherent to the crystals of sodium carbonate, whereas the solid solution at the 1:2 molar ratio shows no such peaks and does not contain the crystals of sodium carbonate.

FIFTH EMBODIMENT

This embodiment provides a gaseous carbon dioxide detection sensor constituted quite in the same manner as in the first embodiment execept for using, as the detection material, a solid solution comprising lithium carbonate and calcium carbonate at a 1:3 molar ratio instead of using the solid solution comprising sodium carbonate and barium carbonate at a 1:1.7 molar ratio.

Figure 12:
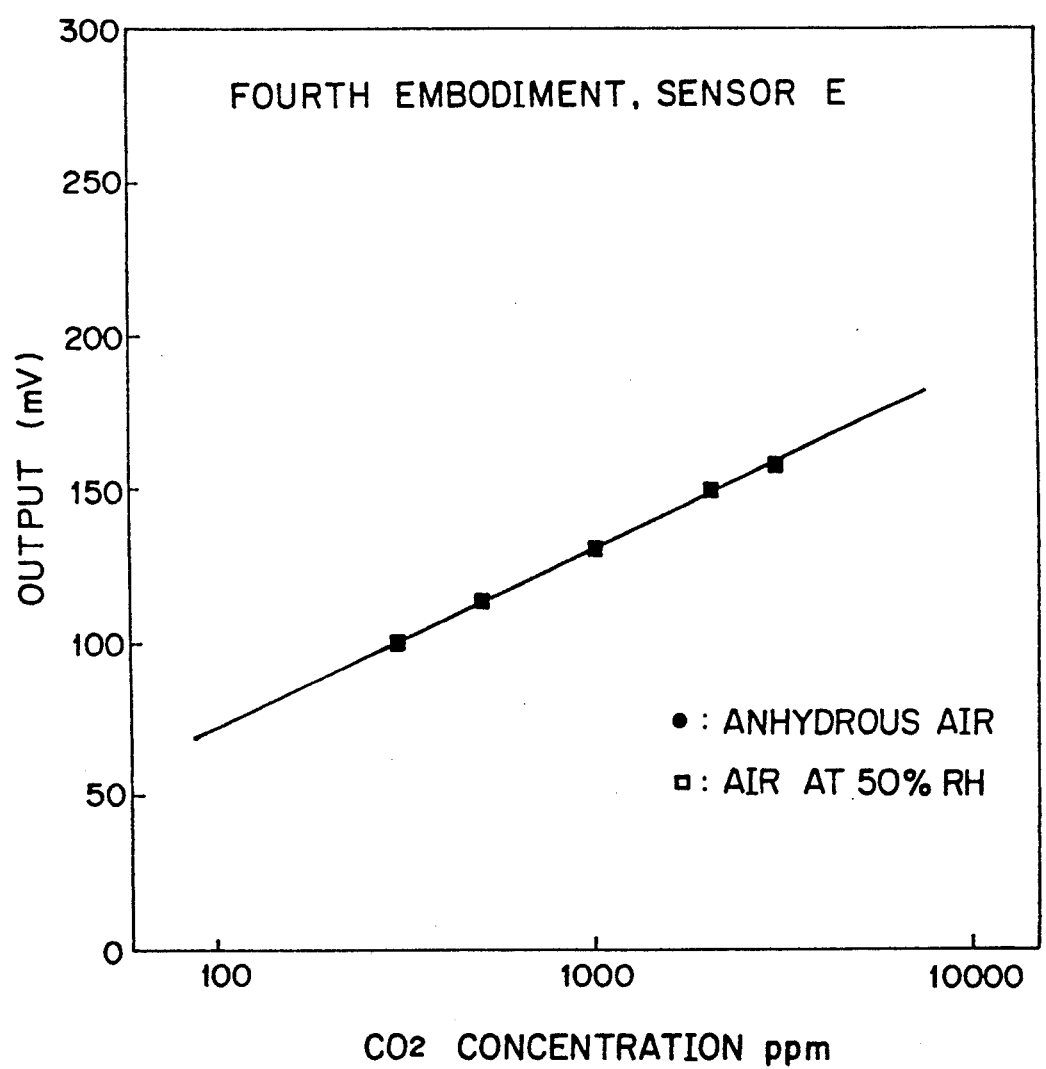
FIG. 12 is a characteristic graph for the detection of gaseous carbon dioxide in humid air and anhydrous air for a gaseous carbon dioxide detection sensor E of a fifth embodiment according to the present invention.

The gaseous carbon dioxide detection sensor E of the fifth embodiment according to the present invention was heated to an element temperature of 550° C. like that in the second embodiment and the characteristic of the electromotive force relative to gaseous carbon dioxide was measured in a humid air and in an anhydrous air. As can be seen from the results shown in FIG. 12, the sensor shows substantially the same characteristics in the humid air as well as in the anhydrous air.

FIFTH COMPARATIVE EMBODIMENT

Figure 13:
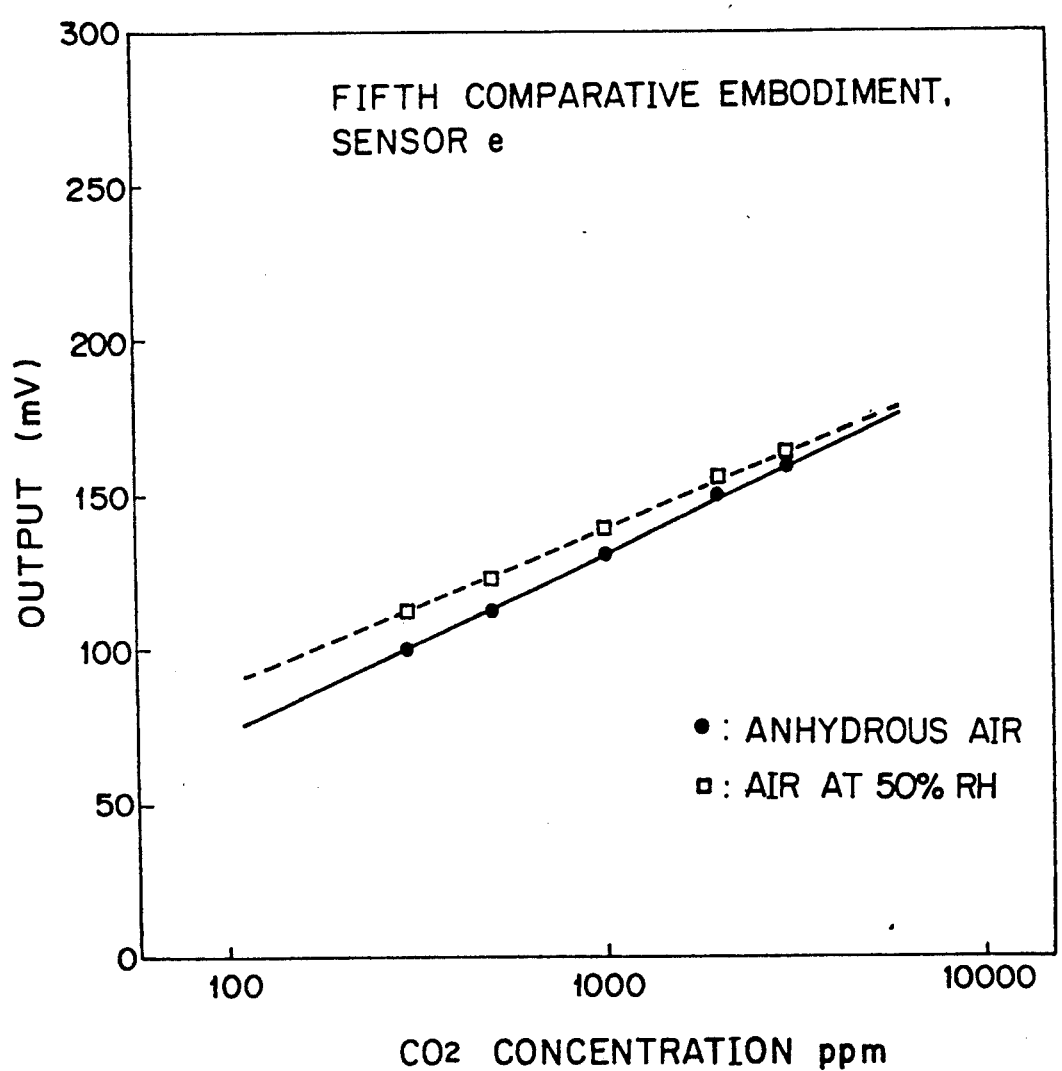
FIG. 13 is a characteristic graph for the detection of gaseous carbon dioxide in humid air and anhydrous air for a gaseous carbon dioxide detection sensor e of a fifth comparative embodiment.

Using a gaseous carbon dioxide detection sensor e constituted quite in the same manner as in the fifth embodiment except for using, as the detection material, a solid solution comprising lithium carbonate and calcium carbonate at a molar ratio of 1:1 instead of 1:3, the characteristic of the electromotive force relative to gaseous carbon dioxide was measured in a humid air and in an anhydrous air in the same manner as in the second embodiment. As can be seen from the results shown in FIG. 13, the output from the gaseous carbon dioxide detection sensor e of the fifth comparative embodiment changes greatly depending on the moisture content in the gas to be detected.

FIFTH REFERENCE EMBODIMENT

Figure 22:
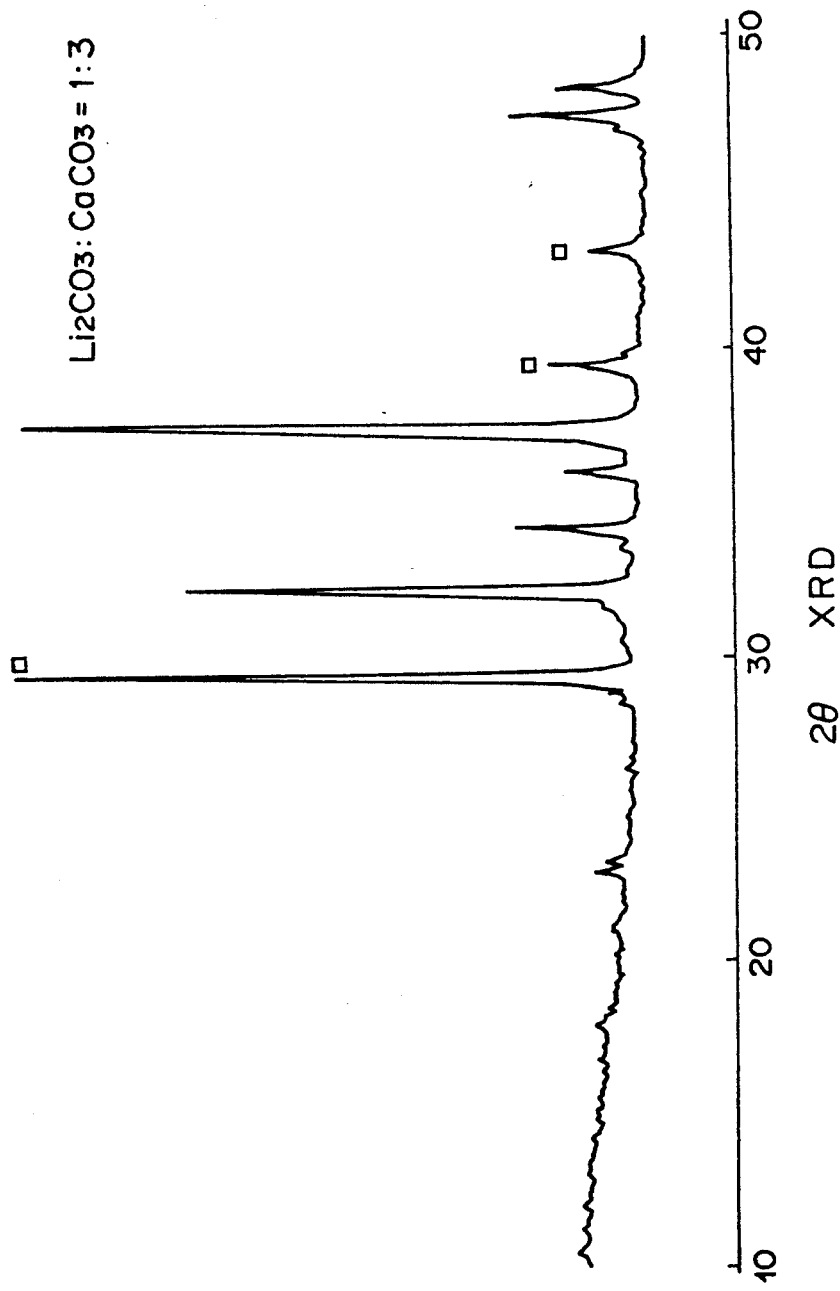
FIG. 22 is an X-ray diffraction chart for a solid solution of lithium carbonate and calcium carbonate at 1:3 molar ratio.
Figure 23:
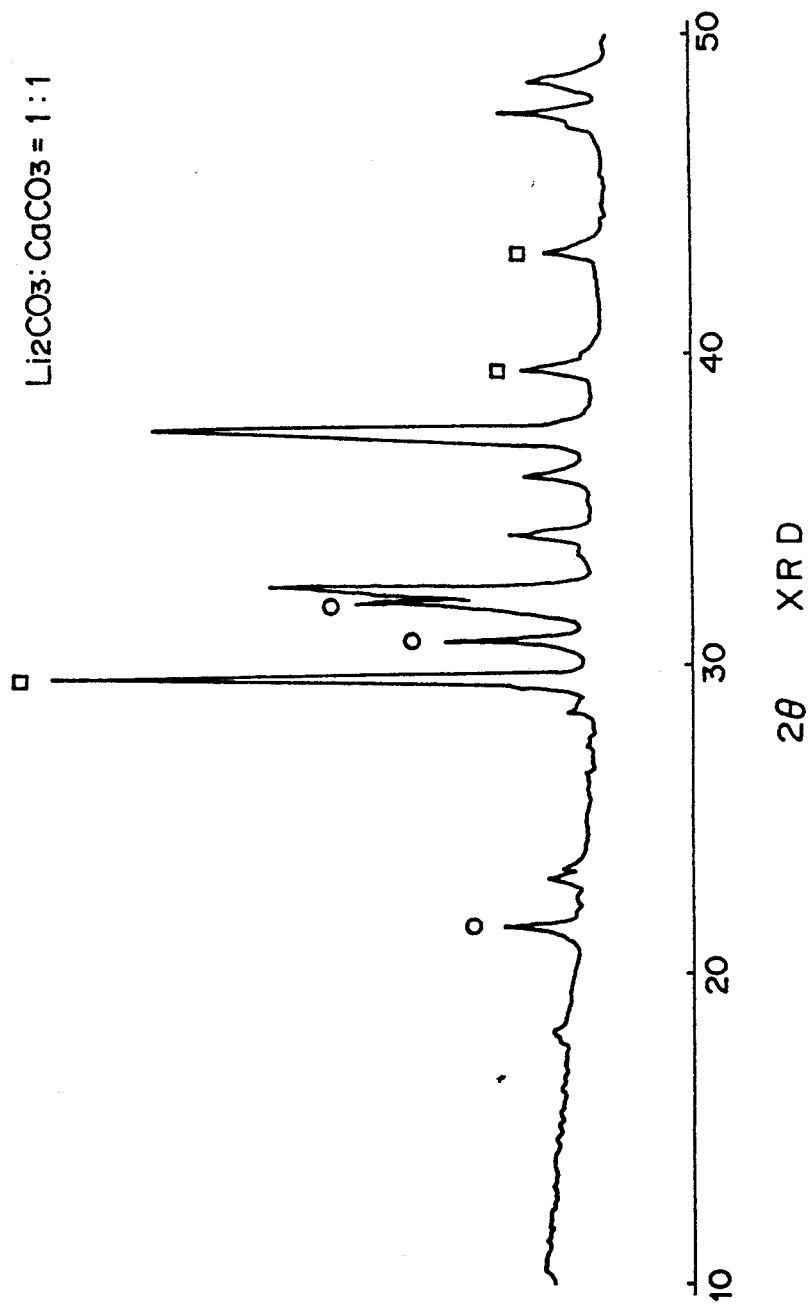
FIG. 23 is an X-ray diffraction chart for a solid solution of lithium carbonate and calcium carbonate at 1:1 molar ratio.
Figure 26:
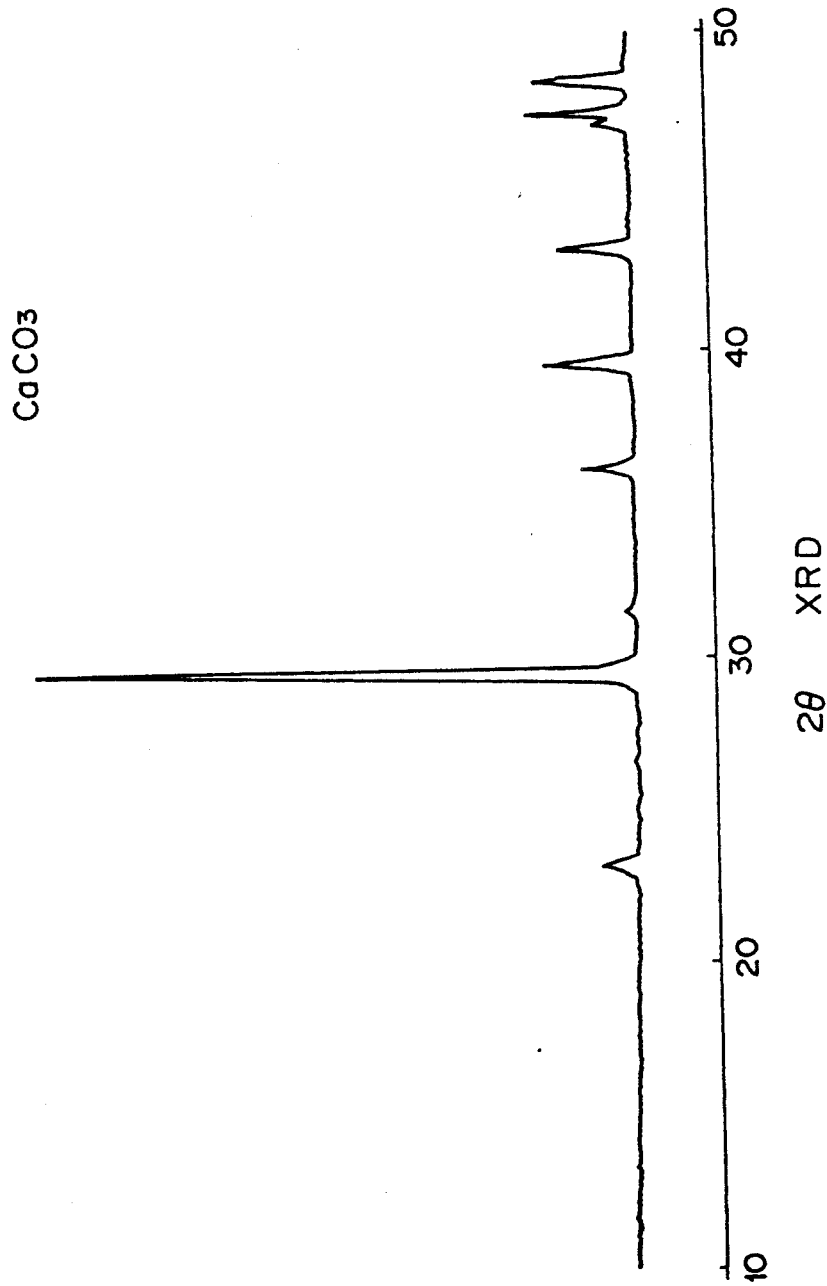
FIG. 26 is an X-ray refraction chart for calcium carbonate.

Crystal structures were analyzed by X-ray diffractiometry for the solid solution comprising lithium carbonate and calcium carbonate at a 1:3 molar ratio used in the fifth embodiment and the solid solution at a 1:1 molar ratio used in the fifth comparative embodiment. The charts are shown in FIG. 22 and FIG. 23. In comparison with a chart for calcium carbonate in FIG. 26 and a chart for lithium carbonate in FIG. 28 for the reference, it can be seen that the solid solution at the 1:1 molar ratio shows peaks inherent to the crystals of sodium carbonate, whereas the solid solution at the 1:33 molar ratio shows no such peaks and does not contain the crystals of lithium carbonate.

As has been described above according to the present invention, since a mixture comprising one mol of an alkali metal carbonate and more than one mol of an alkaline earth metal carbonate, more preferably, a solid solution not containing crystals of the alkali metal carbonate is used as the detection material, a gaseous carbon dioxide detection sensor having characteristics of electromotive force relative to gaseous carbon dioxide less undergoing the effect of moisture content in a gas to be detected and having high sensitivity can be obtained.

We claim:

1. A gaseous carbon dioxide detection sensor comprising a solid ionic conductor having two sides, a detection electrode and a reference electrode positioned on opposite sides of said solid ionic conductor, said detection electrode comprising detection material, said detection material comprising an amount of alkali metal carbonate, and an amount of alkaline earth metal carbonate which is greater than said amount of alkali metal carbonate and which is effective to provide detection material which is effective in said detection electrode to provide a gaseous carbon dioxide detection sensor.

2. A gaseous carbon dioxide detection sensor as defined in claim 1, wherein the detection material is a solid solution comprising the alkali metal carbonate and the alkaline earth metal carbonate and does not contains crystals of the alkali metal carbonate.

3. A gaseous carbon dioxide detection sensor as defined in claim 1, wherein the alkali metal carbonate is at least one of lithium, sodium or potassium carbonates.

4. A gaseous carbon dioxide detection sensor as defined in claim 1, wherein the alkaline earth metal carbonate is at least one of calcium, strontium or barium carbonates.

* * * * *